United States Patent
Greenhalgh et al.

(10) Patent No.: US 9,149,286 B1
(45) Date of Patent: Oct. 6, 2015

(54) GUIDANCE TOOL AND METHOD FOR USE

(75) Inventors: E. Skott Greenhalgh, Gladwyne, PA (US); John-Paul Romano, Chalfont, PA (US); Robert A. Kiefer, Quakertown, PA (US)

(73) Assignee: Flexmedex, LLC, Quakertown, PA (US)

( * ) Notice: Subject to any disclaimer, the term of this patent is extended or adjusted under 35 U.S.C. 154(b) by 0 days.

(21) Appl. No.: 13/296,066

(22) Filed: Nov. 14, 2011

Related U.S. Application Data

(60) Provisional application No. 61/456,806, filed on Nov. 12, 2010.

(51) Int. Cl.
*A61B 17/17* (2006.01)
*A61B 17/16* (2006.01)

(52) U.S. Cl.
CPC ......... *A61B 17/1757* (2013.01); *A61B 17/1671* (2013.01); *A61B 17/17* (2013.01); *A61B 17/1703* (2013.01)

(58) Field of Classification Search
CPC .............. A61B 17/1703; A61B 17/1757
USPC ........ 623/17.11–17.16; 606/96–98, 247–249, 606/279, 87, 86 R, 104; 600/424–425
See application file for complete search history.

(56) References Cited

U.S. PATENT DOCUMENTS

| | | | |
|---|---|---|---|
| 646,119 A | 3/1900 | Clamer et al. | |
| 4,204,531 A | 5/1980 | Aginsky | |
| 4,569,338 A | 2/1986 | Edwards | |
| 4,636,217 A | 1/1987 | Ogilvie et al. | |
| 4,653,489 A | 3/1987 | Tronzo | |
| 4,716,839 A | 1/1988 | Catena | |
| 4,716,893 A | 1/1988 | Fischer et al. | |
| 4,725,264 A | 2/1988 | Glassman | |
| 4,733,665 A | 3/1988 | Palmaz | |
| 4,759,769 A | 7/1988 | Hedman et al. | |
| 4,763,644 A | 8/1988 | Webb | |
| 4,863,476 A | 9/1989 | Shepperd | |
| 4,886,062 A | 12/1989 | Wiktor | |
| 4,911,718 A | 3/1990 | Lee et al. | |
| 4,932,975 A | 6/1990 | Main et al. | |
| 4,941,466 A | 7/1990 | Romano | |
| 4,969,888 A | 11/1990 | Scholten et al. | |

(Continued)

FOREIGN PATENT DOCUMENTS

EP 0734702 10/1996
EP 0758541 2/1997

(Continued)

OTHER PUBLICATIONS

Franklin, I.J. et al., "Uptake of Tetracycline by Aortic Aneurysm Wall and Its Effect on Inflammation and Proteolysis," *Brit. J. Surger*, 86(6):771-775, 1999.

(Continued)

*Primary Examiner* — Todd Manahan
*Assistant Examiner* — Marcela I Shirsat
(74) *Attorney, Agent, or Firm* — Levine Bagade Han LLP

(57) ABSTRACT

Devices and methods for orthopedic support are disclosed. The device can have a first rigid section hingedly attached to a second rigid section. A tunnel through the bone near the implantation target site can be created. The device can be inserted into and pass through and out of the tunnel to the target site.

15 Claims, 29 Drawing Sheets

(56) References Cited

U.S. PATENT DOCUMENTS

| | | |
|---|---|---|
| 5,007,909 A | 4/1991 | Rogozinski |
| 5,015,247 A | 5/1991 | Michelson |
| 5,026,373 A | 6/1991 | Ray et al. |
| 5,059,193 A | 10/1991 | Kuslich |
| 5,108,404 A | 4/1992 | Scholten et al. |
| 5,123,926 A | 6/1992 | Pisharodi |
| 5,139,480 A | 8/1992 | Hickle et al. |
| 5,171,278 A | 12/1992 | Pisharodi |
| 5,217,483 A | 6/1993 | Tower |
| 5,258,031 A | 11/1993 | Salib et al. |
| 5,306,278 A * | 4/1994 | Dahl et al. ............... 606/96 |
| 5,324,295 A * | 6/1994 | Shapiro ............... 606/86 R |
| 5,342,348 A | 8/1994 | Kaplan |
| 5,345,927 A | 9/1994 | Bonutti |
| 5,390,683 A | 2/1995 | Pisharodi |
| 5,390,898 A | 2/1995 | Smedley et al. |
| 5,397,364 A | 3/1995 | Kozak et al. |
| 5,425,773 A | 6/1995 | Boyd et al. |
| 5,454,365 A | 10/1995 | Bonutti |
| 5,458,643 A | 10/1995 | Oka et al. |
| 5,480,442 A | 1/1996 | Bertagnoli |
| 5,484,384 A | 1/1996 | Fearnot |
| 5,496,365 A | 3/1996 | Sgro |
| 5,522,899 A | 6/1996 | Michelson |
| 5,534,002 A | 7/1996 | Brumfield et al. |
| 5,540,690 A | 7/1996 | Miller et al. |
| 5,549,679 A | 8/1996 | Kuslich |
| 5,554,191 A | 9/1996 | Lahille et al. |
| 5,556,413 A | 9/1996 | Lam |
| 5,562,736 A | 10/1996 | Ray et al. |
| 5,562,738 A | 10/1996 | Boyd et al. |
| 5,571,189 A | 11/1996 | Kuslich |
| 5,571,192 A | 11/1996 | Schonhoffer |
| 5,584,831 A | 12/1996 | McKay |
| 5,591,197 A | 1/1997 | Orth et al. |
| 5,593,409 A | 1/1997 | Michelson |
| 5,609,356 A | 3/1997 | Mossi |
| 5,609,635 A | 3/1997 | Michelson |
| 5,643,264 A | 7/1997 | Sherman et al. |
| 5,643,312 A | 7/1997 | Fischell et al. |
| 5,645,560 A | 7/1997 | Crocker et al. |
| 5,649,950 A | 7/1997 | Bourne et al. |
| 5,653,763 A | 8/1997 | Errico et al. |
| 5,658,335 A | 8/1997 | Allen |
| 5,665,122 A | 9/1997 | Kambin |
| 5,669,909 A | 9/1997 | Zdeblick et al. |
| 5,674,295 A | 10/1997 | Ray et al. |
| 5,683,394 A | 11/1997 | Rinner |
| 5,693,100 A | 12/1997 | Pisharodi |
| 5,702,449 A | 12/1997 | McKay |
| 5,702,453 A | 12/1997 | Rabbe et al. |
| 5,741,253 A | 4/1998 | Michelson |
| 5,749,916 A | 5/1998 | Richelsoph |
| 5,772,661 A | 6/1998 | Michelson |
| 5,776,181 A | 7/1998 | Lee et al. |
| 5,776,197 A | 7/1998 | Rabbe et al. |
| 5,776,198 A | 7/1998 | Rabbe et al. |
| 5,776,199 A | 7/1998 | Michelson |
| 5,782,832 A | 7/1998 | Larsen et al. |
| 5,782,903 A | 7/1998 | Wiktor |
| 5,785,710 A | 7/1998 | Michelson |
| 5,800,520 A | 9/1998 | Fogarty et al. |
| 5,824,054 A | 10/1998 | Khosravi et al. |
| 5,824,093 A | 10/1998 | Ray et al. |
| 5,827,289 A | 10/1998 | Reiley et al. |
| 5,827,321 A | 10/1998 | Roubin et al. |
| 5,853,419 A | 12/1998 | Imran |
| 5,861,025 A | 1/1999 | Boudghene et al. |
| 5,863,284 A | 1/1999 | Klein |
| 5,865,848 A | 2/1999 | Baker |
| 5,972,015 A | 10/1999 | Scribner et al. |
| 5,980,522 A | 11/1999 | Koros et al. |
| 5,980,550 A | 11/1999 | Eder et al. |
| 5,984,957 A | 11/1999 | Laptewicz et al. |
| 6,001,130 A | 12/1999 | Bryan et al. |
| 6,019,765 A | 2/2000 | Thornhill et al. |
| 6,019,792 A | 2/2000 | Cauthen |
| 6,022,376 A | 2/2000 | Assell et al. |
| 6,025,104 A | 2/2000 | Fuller et al. |
| 6,027,527 A | 2/2000 | Asano et al. |
| 6,036,719 A | 3/2000 | Meilus |
| 6,039,761 A | 3/2000 | Li et al. |
| 6,045,579 A | 4/2000 | Hochshuler et al. |
| 6,053,916 A | 4/2000 | Moore |
| 6,066,154 A | 5/2000 | Reiley et al. |
| 6,077,246 A | 6/2000 | Kullas et al. |
| 6,080,193 A | 6/2000 | Hochshuler et al. |
| 6,083,522 A | 7/2000 | Chu et al. |
| 6,086,610 A | 7/2000 | Duerig et al. |
| 6,090,143 A | 7/2000 | Meriwether et al. |
| 6,102,950 A | 8/2000 | Vaccaro |
| 6,113,639 A | 9/2000 | Ray et al. |
| 6,126,689 A | 10/2000 | Brett |
| 6,127,597 A | 10/2000 | Beyar et al. |
| 6,129,763 A | 10/2000 | Chauvin et al. |
| 6,132,465 A | 10/2000 | Ray et al. |
| 6,140,452 A | 10/2000 | Felt et al. |
| 6,146,417 A | 11/2000 | Ischinger |
| 6,159,244 A | 12/2000 | Suddaby |
| 6,159,245 A | 12/2000 | Meriwether et al. |
| 6,168,616 B1 | 1/2001 | Brown, III |
| 6,171,312 B1 | 1/2001 | Beaty |
| 6,176,882 B1 | 1/2001 | Biedermann et al. |
| 6,179,874 B1 | 1/2001 | Cauthen |
| 6,183,506 B1 | 2/2001 | Penn et al. |
| 6,183,517 B1 | 2/2001 | Suddaby |
| 6,193,757 B1 | 2/2001 | Foley et al. |
| 6,206,910 B1 | 3/2001 | Berry et al. |
| 6,206,924 B1 | 3/2001 | Timm |
| 6,224,595 B1 | 5/2001 | Michelson |
| 6,224,603 B1 | 5/2001 | Marino |
| 6,224,604 B1 | 5/2001 | Suddaby |
| 6,224,607 B1 | 5/2001 | Michelson |
| 6,235,043 B1 | 5/2001 | Reiley et al. |
| 6,241,734 B1 | 6/2001 | Scribner et al. |
| 6,245,101 B1 | 6/2001 | Drasler et al. |
| 6,245,107 B1 | 6/2001 | Ferree |
| 6,248,110 B1 | 6/2001 | Reiley et al. |
| 6,280,456 B1 | 8/2001 | Scribner et al. |
| 6,287,332 B1 | 9/2001 | Bolz et al. |
| 6,293,967 B1 | 9/2001 | Shanley |
| 6,302,914 B1 | 10/2001 | Michelson |
| 6,332,895 B1 | 12/2001 | Suddaby |
| 6,371,989 B1 | 4/2002 | Chauvin et al. |
| 6,395,031 B1 | 5/2002 | Foley et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,419,704 B1 | 7/2002 | Ferree |
| 6,419,705 B1 | 7/2002 | Erickson |
| 6,423,083 B2 | 7/2002 | Reiley et al. |
| 6,425,916 B1 | 7/2002 | Garrison et al. |
| 6,425,919 B1 | 7/2002 | Lambrecht |
| 6,428,569 B1 | 8/2002 | Brown |
| 6,432,107 B1 | 8/2002 | Ferree |
| 6,436,098 B1 | 8/2002 | Michelson |
| 6,436,140 B1 | 8/2002 | Liu et al. |
| 6,440,168 B1 | 8/2002 | Cauthen |
| 6,447,544 B1 | 9/2002 | Michelson |
| 6,447,546 B1 | 9/2002 | Bramlet et al. |
| 6,447,547 B1 | 9/2002 | Michelson |
| 6,451,025 B1 | 9/2002 | Jervis |
| 6,454,804 B1 | 9/2002 | Ferree |
| 6,468,301 B1 | 10/2002 | Amplatz et al. |
| 6,468,302 B2 | 10/2002 | Coc et al. |
| 6,478,823 B1 | 11/2002 | Michelson |
| 6,482,235 B1 | 11/2002 | Lambrecht et al. |
| 6,488,710 B2 | 12/2002 | Besselink |
| 6,491,724 B1 | 12/2002 | Ferree |
| 6,494,883 B1 | 12/2002 | Ferree |
| 6,508,820 B2 | 1/2003 | Bales |
| 6,508,839 B1 | 1/2003 | Lambrecht et al. |
| 6,514,255 B1 | 2/2003 | Ferree |
| 6,520,991 B2 | 2/2003 | Huene |

(56) References Cited

U.S. PATENT DOCUMENTS

| | | |
|---|---|---|
| 6,533,817 B1 | 3/2003 | Norton et al. |
| 6,554,833 B2 | 4/2003 | Levy et al. |
| 6,562,074 B2 | 5/2003 | Gerbec et al. |
| 6,582,431 B1 | 6/2003 | Ray |
| 6,582,467 B1 | 6/2003 | Teitelbaum et al. |
| 6,585,770 B1 | 7/2003 | White et al. |
| 6,592,589 B2 | 7/2003 | Hajianpour |
| 6,592,625 B2 | 7/2003 | Cauthen |
| 6,595,998 B2 | 7/2003 | Johnson et al. |
| 6,602,291 B1 | 8/2003 | Ray et al. |
| 6,607,530 B1 * | 8/2003 | Carl et al. ................ 606/914 |
| 6,607,544 B1 | 8/2003 | Boucher et al. |
| 6,613,054 B2 | 9/2003 | Scribner et al. |
| 6,623,505 B2 | 9/2003 | Scribner et al. |
| 6,641,587 B2 | 11/2003 | Scribner et al. |
| 6,641,614 B1 | 11/2003 | Wagner et al. |
| 6,645,213 B2 | 11/2003 | Sand et al. |
| 6,645,247 B2 | 11/2003 | Ferree |
| 6,648,917 B2 | 11/2003 | Gerbec et al. |
| 6,648,918 B2 | 11/2003 | Ferree |
| 6,648,920 B2 | 11/2003 | Ferree |
| 6,652,584 B2 | 11/2003 | Michelson |
| 6,656,178 B1 | 12/2003 | Veldhuizen et al. |
| 6,663,647 B2 | 12/2003 | Reiley et al. |
| 6,666,891 B2 | 12/2003 | Boehm, Jr. et al. |
| 6,676,665 B2 | 1/2004 | Foley et al. |
| 6,679,915 B1 | 1/2004 | Cauthen |
| 6,685,695 B2 | 2/2004 | Ferree |
| 6,695,760 B1 | 2/2004 | Winkler et al. |
| 6,706,068 B2 | 3/2004 | Ferree |
| 6,706,070 B1 | 3/2004 | Wagner et al. |
| 6,709,458 B2 | 3/2004 | Michelson |
| 6,712,853 B2 | 3/2004 | Kuslich |
| 6,716,216 B1 | 4/2004 | Boucher et al. |
| 6,716,247 B2 | 4/2004 | Michelson |
| 6,719,773 B1 | 4/2004 | Boucher et al. |
| 6,723,126 B1 | 4/2004 | Berry |
| 6,726,691 B2 | 4/2004 | Osorio et al. |
| 6,733,535 B2 | 5/2004 | Michelson |
| 6,740,090 B1 | 5/2004 | Cragg et al. |
| 6,743,255 B2 | 6/2004 | Ferree |
| 6,746,451 B2 | 6/2004 | Middleton et al. |
| 6,758,863 B2 | 7/2004 | Estes et al. |
| 6,793,656 B1 | 9/2004 | Mathews |
| 6,793,679 B2 | 9/2004 | Michelson |
| 6,808,537 B2 | 10/2004 | Michelson |
| 6,814,756 B1 | 11/2004 | Michelson |
| 6,830,589 B2 | 12/2004 | Erickson |
| 6,852,115 B2 | 2/2005 | Kinnett |
| 6,852,123 B2 | 2/2005 | Brown |
| 6,852,129 B2 | 2/2005 | Gerbec et al. |
| 6,863,673 B2 | 3/2005 | Gerbec et al. |
| 6,893,464 B2 | 5/2005 | Kiester |
| 6,899,716 B2 | 5/2005 | Baldwin |
| 6,899,719 B2 | 5/2005 | Reiley et al. |
| 6,921,264 B2 | 7/2005 | Mayer et al. |
| 6,923,813 B2 | 8/2005 | Phillips et al. |
| 6,923,830 B2 | 8/2005 | Michelson |
| 6,936,065 B2 | 8/2005 | Khan et al. |
| 6,936,070 B1 | 8/2005 | Muhanna |
| 6,948,223 B2 | 9/2005 | Shortt |
| 6,953,477 B2 | 10/2005 | Berry |
| 6,955,691 B2 | 10/2005 | Chae et al. |
| 6,960,215 B2 | 11/2005 | Olson et al. |
| 6,962,606 B2 | 11/2005 | Michelson |
| 6,981,981 B2 | 1/2006 | Reiley et al. |
| 7,008,453 B1 | 3/2006 | Michelson |
| 7,018,415 B1 | 3/2006 | McKay |
| 7,018,416 B2 | 3/2006 | Hanson et al. |
| 7,056,321 B2 | 6/2006 | Pagliuca et al. |
| 7,060,073 B2 | 6/2006 | Frey et al. |
| 7,066,961 B2 | 6/2006 | Michelson |
| 7,077,864 B2 | 7/2006 | Byrd, III et al. |
| 7,087,055 B2 | 8/2006 | Lim et al. |
| 7,094,257 B2 | 8/2006 | Mujwid et al. |
| 7,097,648 B1 | 8/2006 | Globerman et al. |
| 7,112,206 B2 | 9/2006 | Michelson |
| 7,118,598 B2 | 10/2006 | Michelson |
| 7,135,043 B2 | 11/2006 | Nakahara et al. |
| 7,166,110 B2 | 1/2007 | Yundt |
| 7,201,751 B2 | 4/2007 | Zucherman et al. |
| 7,201,775 B2 | 4/2007 | Gorensek et al. |
| 7,204,853 B2 | 4/2007 | Gordon et al. |
| 7,211,112 B2 | 5/2007 | Baynham et al. |
| 7,212,480 B2 | 5/2007 | Shoji et al. |
| 7,223,292 B2 | 5/2007 | Messerli et al. |
| 7,226,475 B2 | 6/2007 | Lenz et al. |
| 7,226,481 B2 | 6/2007 | Kuslich |
| 7,226,483 B2 | 6/2007 | Gerber et al. |
| 7,238,186 B2 | 7/2007 | Zdeblick et al. |
| 7,241,297 B2 | 7/2007 | Shaolian et al. |
| 7,241,303 B2 | 7/2007 | Reiss et al. |
| 7,300,440 B2 | 11/2007 | Zdeblick et al. |
| 7,309,338 B2 | 12/2007 | Cragg |
| 7,311,713 B2 | 12/2007 | Johnson et al. |
| 7,316,714 B2 | 1/2008 | Gordon et al. |
| 7,318,826 B2 | 1/2008 | Teitelbaum et al. |
| 7,396,360 B2 * | 7/2008 | Lieberman ................ 606/247 |
| 7,431,735 B2 | 10/2008 | Liu et al. |
| 7,452,371 B2 | 11/2008 | Pavcnik et al. |
| 7,503,933 B2 | 3/2009 | Michelson |
| 7,507,241 B2 | 3/2009 | Levy et al. |
| 7,582,106 B2 | 9/2009 | Teitelbaum et al. |
| 7,601,172 B2 | 10/2009 | Segal et al. |
| 7,618,457 B2 | 11/2009 | Hudgins |
| 7,621,950 B1 | 11/2009 | Globerman et al. |
| 7,722,674 B1 | 5/2010 | Grotz |
| 7,749,228 B2 | 7/2010 | Lieberman |
| 7,763,028 B2 | 7/2010 | Lim et al. |
| 7,828,849 B2 | 11/2010 | Lim |
| 7,837,734 B2 | 11/2010 | Zucherman et al. |
| 7,867,233 B2 | 1/2011 | Shaolian et al. |
| 7,875,035 B2 | 1/2011 | Boucher et al. |
| 7,879,036 B2 | 2/2011 | Biedermann et al. |
| 7,879,082 B2 | 2/2011 | Brown |
| 8,007,498 B2 | 8/2011 | Mische |
| 8,105,382 B2 | 1/2012 | Olmos et al. |
| 8,246,622 B2 | 8/2012 | Siegal et al. |
| 2001/0007956 A1 | 7/2001 | Letac et al. |
| 2001/0034552 A1 | 10/2001 | Young et al. |
| 2002/0007218 A1 | 1/2002 | Cauthen |
| 2002/0010511 A1 | 1/2002 | Michelson |
| 2002/0022887 A1 | 2/2002 | Huene |
| 2002/0032444 A1 | 3/2002 | Mische |
| 2002/0052656 A1 | 5/2002 | Michelson |
| 2002/0068911 A1 | 6/2002 | Chan |
| 2002/0068939 A1 | 6/2002 | Levy et al. |
| 2002/0068975 A1 | 6/2002 | Teitelbaum et al. |
| 2002/0068976 A1 | 6/2002 | Jackson |
| 2002/0068977 A1 | 6/2002 | Jackson |
| 2002/0082598 A1 | 6/2002 | Teitelbaum |
| 2002/0082600 A1 | 6/2002 | Shaolian et al. |
| 2002/0091390 A1 | 7/2002 | Michelson |
| 2002/0095155 A1 | 7/2002 | Michelson |
| 2002/0099378 A1 | 7/2002 | Michelson |
| 2002/0111688 A1 | 8/2002 | Cauthen |
| 2002/0120337 A1 | 8/2002 | Cauthen |
| 2002/0123807 A1 | 9/2002 | Cauthen |
| 2002/0128713 A1 | 9/2002 | Ferree |
| 2002/0138077 A1 | 9/2002 | Ferree |
| 2002/0138133 A1 | 9/2002 | Lenz et al. |
| 2002/0138144 A1 | 9/2002 | Michelson |
| 2002/0143401 A1 | 10/2002 | Michelson |
| 2002/0151896 A1 | 10/2002 | Ferree |
| 2002/0151980 A1 | 10/2002 | Cauthen |
| 2002/0156530 A1 | 10/2002 | Lambrecht et al. |
| 2002/0161367 A1 | 10/2002 | Ferree |
| 2002/0161373 A1 | 10/2002 | Osorio et al. |
| 2002/0165542 A1 | 11/2002 | Ferree |
| 2002/0189622 A1 | 12/2002 | Cauthen et al. |
| 2002/0198526 A1 | 12/2002 | Shaolian et al. |
| 2003/0004511 A1 | 1/2003 | Ferree |
| 2003/0004574 A1 | 1/2003 | Ferree |
| 2003/0009227 A1 | 1/2003 | Lambrecht et al. |

(56) References Cited

U.S. PATENT DOCUMENTS

| | | |
|---|---|---|
| 2003/0014118 A1 | 1/2003 | Lambrecht et al. |
| 2003/0026788 A1 | 2/2003 | Ferree |
| 2003/0032963 A1 | 2/2003 | Reiss et al. |
| 2003/0040796 A1 | 2/2003 | Ferree |
| 2003/0040798 A1 | 2/2003 | Michelson |
| 2003/0050701 A1 | 3/2003 | Michelson |
| 2003/0065394 A1 | 4/2003 | Michelson |
| 2003/0065396 A1 | 4/2003 | Michelson |
| 2003/0074076 A1 | 4/2003 | Ferree et al. |
| 2003/0078579 A1 | 4/2003 | Ferree |
| 2003/0088249 A1 | 5/2003 | Furderer |
| 2003/0120345 A1 | 6/2003 | Cauthen |
| 2003/0125748 A1 | 7/2003 | Li et al. |
| 2003/0125807 A1 | 7/2003 | Lambrecht et al. |
| 2003/0135220 A1 | 7/2003 | Cauthen |
| 2003/0135279 A1 | 7/2003 | Michelson |
| 2003/0149482 A1 | 8/2003 | Michelson |
| 2003/0153976 A1 | 8/2003 | Cauthen et al. |
| 2003/0158553 A1 | 8/2003 | Michelson |
| 2003/0158604 A1 | 8/2003 | Cauthen et al. |
| 2003/0163200 A1 | 8/2003 | Cauthen |
| 2003/0181979 A1 | 9/2003 | Ferree |
| 2003/0181980 A1 | 9/2003 | Berry et al. |
| 2003/0181983 A1 | 9/2003 | Cauthen |
| 2003/0187507 A1 | 10/2003 | Cauthen |
| 2003/0187508 A1 | 10/2003 | Cauthen |
| 2003/0191536 A1 | 10/2003 | Ferree |
| 2003/0195514 A1 | 10/2003 | Trieu et al. |
| 2003/0195630 A1 | 10/2003 | Ferree |
| 2003/0195631 A1 | 10/2003 | Ferree |
| 2003/0199979 A1 | 10/2003 | McGuckin |
| 2003/0199981 A1 | 10/2003 | Ferree |
| 2003/0204260 A1 | 10/2003 | Ferree |
| 2003/0208270 A9 | 11/2003 | Michelson |
| 2003/0220643 A1 | 11/2003 | Ferree |
| 2003/0220650 A1 | 11/2003 | Major et al. |
| 2003/0220690 A1 | 11/2003 | Cauthen |
| 2003/0220693 A1 | 11/2003 | Cauthen |
| 2003/0220694 A1 | 11/2003 | Cauthen |
| 2003/0233097 A1 | 12/2003 | Ferree |
| 2003/0233148 A1 | 12/2003 | Ferree |
| 2003/0233188 A1 | 12/2003 | Jones |
| 2003/0236520 A1 | 12/2003 | Lim et al. |
| 2004/0002759 A1 | 1/2004 | Ferree |
| 2004/0002760 A1 | 1/2004 | Boyd et al. |
| 2004/0002769 A1 | 1/2004 | Ferree |
| 2004/0006341 A1 | 1/2004 | Shaolian et al. |
| 2004/0006344 A1 | 1/2004 | Nguyen et al. |
| 2004/0010315 A1 | 1/2004 | Song |
| 2004/0010318 A1 | 1/2004 | Ferree |
| 2004/0019386 A1 | 1/2004 | Ferree |
| 2004/0024400 A1 | 2/2004 | Michelson |
| 2004/0024459 A1 | 2/2004 | Ferree |
| 2004/0024460 A1 | 2/2004 | Ferree |
| 2004/0024461 A1 | 2/2004 | Ferree |
| 2004/0024462 A1 | 2/2004 | Ferree et al. |
| 2004/0024469 A1 | 2/2004 | Ferree |
| 2004/0024471 A1 | 2/2004 | Ferree |
| 2004/0028718 A1 | 2/2004 | Ferree |
| 2004/0030387 A1 | 2/2004 | Landry et al. |
| 2004/0030389 A1 | 2/2004 | Ferree |
| 2004/0030390 A1 | 2/2004 | Ferree |
| 2004/0030391 A1 | 2/2004 | Ferree |
| 2004/0030398 A1 | 2/2004 | Ferree |
| 2004/0034357 A1 | 2/2004 | Beane et al. |
| 2004/0044410 A1 | 3/2004 | Ferree et al. |
| 2004/0049289 A1 | 3/2004 | Tordy et al. |
| 2004/0059418 A1 | 3/2004 | McKay et al. |
| 2004/0059419 A1 | 3/2004 | Michelson |
| 2004/0059429 A1 | 3/2004 | Amin et al. |
| 2004/0068259 A1 | 4/2004 | Michelson |
| 2004/0082954 A1 | 4/2004 | Teitelbaum et al. |
| 2004/0082961 A1 | 4/2004 | Teitelbaum |
| 2004/0087950 A1 | 5/2004 | Teitelbaum |
| 2004/0092933 A1 | 5/2004 | Shaolian et al. |
| 2004/0092988 A1 | 5/2004 | Shaolian et al. |
| 2004/0097927 A1 | 5/2004 | Yeung et al. |
| 2004/0111108 A1 | 6/2004 | Farnan |
| 2004/0133229 A1 | 7/2004 | Lambrecht et al. |
| 2004/0133280 A1 | 7/2004 | Trieu |
| 2004/0138673 A1 | 7/2004 | Lambrecht et al. |
| 2004/0153064 A1 | 8/2004 | Foley et al. |
| 2004/0153065 A1 | 8/2004 | Lim |
| 2004/0153146 A1 | 8/2004 | Lashinski et al. |
| 2004/0167625 A1 | 8/2004 | Beyar et al. |
| 2005/0010292 A1 | 1/2005 | Carrasco |
| 2005/0015152 A1 | 1/2005 | Sweeney |
| 2005/0033431 A1 | 2/2005 | Gordon et al. |
| 2005/0038512 A1 | 2/2005 | Michelson |
| 2005/0043796 A1 | 2/2005 | Grant et al. |
| 2005/0070911 A1 | 3/2005 | Carrison et al. |
| 2005/0080422 A1 | 4/2005 | Otte et al. |
| 2005/0085910 A1 | 4/2005 | Sweeney |
| 2005/0107863 A1 | 5/2005 | Brown |
| 2005/0113919 A1 | 5/2005 | Cragg et al. |
| 2005/0113928 A1 | 5/2005 | Cragg et al. |
| 2005/0119561 A1 * | 6/2005 | Kienzle ............ 600/425 |
| 2005/0143827 A1 | 6/2005 | Globerman et al. |
| 2005/0182463 A1 | 8/2005 | Hunter et al. |
| 2005/0187558 A1 | 8/2005 | Johnson et al. |
| 2005/0209698 A1 | 9/2005 | Gordon et al. |
| 2005/0228391 A1 | 10/2005 | Levy et al. |
| 2005/0240188 A1 | 10/2005 | Chow et al. |
| 2005/0249776 A1 | 11/2005 | Chen et al. |
| 2005/0261768 A1 | 11/2005 | Trieu |
| 2005/0278023 A1 | 12/2005 | Zwirkoski |
| 2005/0278026 A1 | 12/2005 | Gordon et al. |
| 2005/0278036 A1 | 12/2005 | Leonard et al. |
| 2006/0004455 A1 | 1/2006 | Leonard et al. |
| 2006/0015184 A1 | 1/2006 | Winterbottom et al. |
| 2006/0036241 A1 | 2/2006 | Siegal |
| 2006/0052788 A1 | 3/2006 | Thelen et al. |
| 2006/0052870 A1 | 3/2006 | Ferree |
| 2006/0058807 A1 | 3/2006 | Landry et al. |
| 2006/0058876 A1 | 3/2006 | McKinley |
| 2006/0058880 A1 | 3/2006 | Wysocki et al. |
| 2006/0085069 A1 | 4/2006 | Kim |
| 2006/0089715 A1 | 4/2006 | Truckai et al. |
| 2006/0100706 A1 | 5/2006 | Shadduck et al. |
| 2006/0106460 A1 | 5/2006 | Messerli et al. |
| 2006/0122701 A1 | 6/2006 | Kiester |
| 2006/0142859 A1 | 6/2006 | McLuen |
| 2006/0149239 A1 | 7/2006 | Winslow et al. |
| 2006/0149349 A1 | 7/2006 | Garbe |
| 2006/0149385 A1 | 7/2006 | McKay |
| 2006/0161261 A1 | 7/2006 | Brown et al. |
| 2006/0178694 A1 | 8/2006 | Greenhalgh et al. |
| 2006/0184188 A1 | 8/2006 | Li et al. |
| 2006/0200166 A1 | 9/2006 | Hanson et al. |
| 2006/0206207 A1 | 9/2006 | Dryer et al. |
| 2006/0235423 A1 | 10/2006 | Cantu |
| 2006/0241764 A1 | 10/2006 | Michelson |
| 2006/0253201 A1 | 11/2006 | McLuen |
| 2006/0264968 A1 | 11/2006 | Frey et al. |
| 2006/0271061 A1 | 11/2006 | Beyar et al. |
| 2006/0287725 A1 | 12/2006 | Miller |
| 2006/0287726 A1 | 12/2006 | Segal et al. |
| 2006/0287727 A1 | 12/2006 | Segal et al. |
| 2006/0287729 A1 | 12/2006 | Segal et al. |
| 2006/0287730 A1 | 12/2006 | Segal et al. |
| 2007/0027363 A1 | 2/2007 | Gannoe et al. |
| 2007/0032791 A1 | 2/2007 | Greenhalgh |
| 2007/0043440 A1 | 2/2007 | William et al. |
| 2007/0055375 A1 | 3/2007 | Ferree |
| 2007/0055377 A1 | 3/2007 | Hanson et al. |
| 2007/0067034 A1 | 3/2007 | Chirico et al. |
| 2007/0093897 A1 | 4/2007 | Gerbec et al. |
| 2007/0093899 A1 | 4/2007 | Dutoit et al. |
| 2007/0112428 A1 | 5/2007 | Lancial |
| 2007/0118222 A1 | 5/2007 | Lang |
| 2007/0162044 A1 * | 7/2007 | Marino ............ 606/96 |
| 2007/0162135 A1 | 7/2007 | Segal et al. |
| 2007/0173824 A1 | 7/2007 | Rosen |
| 2007/0173830 A1 | 7/2007 | Rosen |

(56) References Cited

U.S. PATENT DOCUMENTS

| | | |
|---|---|---|
| 2007/0173939 A1 | 7/2007 | Kim et al. |
| 2007/0173940 A1 | 7/2007 | Hestad et al. |
| 2007/0208423 A1 | 9/2007 | Messerli et al. |
| 2007/0213717 A1 | 9/2007 | Trieu et al. |
| 2007/0225703 A1 | 9/2007 | Schmitz et al. |
| 2007/0233260 A1 | 10/2007 | Cragg |
| 2007/0239162 A1 | 10/2007 | Bhatnagar et al. |
| 2007/0244485 A1 | 10/2007 | Greenhalgh et al. |
| 2007/0255408 A1 | 11/2007 | Castleman et al. |
| 2007/0255409 A1 | 11/2007 | Dickson et al. |
| 2007/0260270 A1 | 11/2007 | Assell et al. |
| 2007/0260315 A1 | 11/2007 | Foley et al. |
| 2007/0270956 A1 | 11/2007 | Heinz |
| 2007/0270968 A1 | 11/2007 | Baynham et al. |
| 2007/0276377 A1 | 11/2007 | Yundt |
| 2007/0288028 A1 | 12/2007 | Gorensek et al. |
| 2008/0015694 A1 | 1/2008 | Tribus |
| 2008/0021558 A1 | 1/2008 | Thramann |
| 2008/0021559 A1 | 1/2008 | Thramann |
| 2008/0071356 A1 | 3/2008 | Greenhalgh et al. |
| 2008/0077150 A1 | 3/2008 | Nguyen |
| 2008/0140082 A1 | 6/2008 | Erdem et al. |
| 2008/0140207 A1 | 6/2008 | Olmos et al. |
| 2008/0147193 A1 | 6/2008 | Matthis et al. |
| 2008/0147194 A1 | 6/2008 | Grotz et al. |
| 2008/0183204 A1 | 7/2008 | Greenhalgh et al. |
| 2008/0188941 A1 | 8/2008 | Grotz |
| 2008/0221687 A1 | 9/2008 | Viker |
| 2008/0243254 A1 | 10/2008 | Butler |
| 2008/0249625 A1 | 10/2008 | Waugh et al. |
| 2008/0294205 A1 | 11/2008 | Greenhalgh et al. |
| 2008/0312743 A1 | 12/2008 | Vila et al. |
| 2008/0312744 A1* | 12/2008 | Vresilovic et al. ......... 623/17.16 |
| 2009/0018524 A1 | 1/2009 | Greenhalgh et al. |
| 2009/0024204 A1 | 1/2009 | Greenhalgh et al. |
| 2009/0024217 A1 | 1/2009 | Levy et al. |
| 2009/0054991 A1 | 2/2009 | Biyani et al. |
| 2009/0076511 A1 | 3/2009 | Osman |
| 2009/0149956 A1 | 6/2009 | Greenhalgh et al. |
| 2009/0163918 A1 | 6/2009 | Levy et al. |
| 2009/0182431 A1 | 7/2009 | Butler et al. |
| 2009/0198338 A1 | 8/2009 | Phan |
| 2009/0234398 A1 | 9/2009 | Chirico et al. |
| 2009/0240335 A1 | 9/2009 | Arcenio et al. |
| 2009/0318928 A1 | 12/2009 | Purcell et al. |
| 2010/0004750 A1 | 1/2010 | Segal et al. |
| 2010/0004751 A1 | 1/2010 | Segal et al. |
| 2010/0016905 A1 | 1/2010 | Greenhalgh et al. |
| 2010/0082109 A1 | 4/2010 | Greenhalgh et al. |
| 2010/0125274 A1 | 5/2010 | Greenhalgh et al. |
| 2010/0262147 A1 | 10/2010 | Siegal et al. |
| 2010/0292796 A1 | 11/2010 | Greenhalgh et al. |
| 2010/0324560 A1* | 12/2010 | Suda ........................... 606/79 |
| 2011/0029083 A1* | 2/2011 | Hynes et al. ............... 623/17.16 |
| 2011/0054621 A1 | 3/2011 | Lim |
| 2011/0087296 A1 | 4/2011 | Reiley et al. |
| 2011/0106260 A1 | 5/2011 | Laurence et al. |
| 2011/0125266 A1 | 5/2011 | Rodgers et al. |
| 2011/0184519 A1 | 7/2011 | Trieu |
| 2011/0257684 A1 | 10/2011 | Sankaran |
| 2011/0282387 A1 | 11/2011 | Suh et al. |
| 2011/0319898 A1 | 12/2011 | O'Neil et al. |
| 2011/0320000 A1 | 12/2011 | O'Neil et al. |

FOREIGN PATENT DOCUMENTS

| | | |
|---|---|---|
| EP | 1804733 | 7/2007 |
| FR | 2874814 | 11/2007 |
| FR | 2900814 | 11/2007 |
| JP | 2000-210315 | 8/2000 |
| JP | 2002-535080 | 10/2002 |
| JP | 2003-512887 | 4/2003 |
| JP | 2004-511297 | 4/2004 |
| JP | 2004-531355 | 10/2004 |
| JP | 2004-321348 | 11/2004 |
| SU | 662082 | 5/1979 |
| WO | WO 88/03781 | 6/1988 |
| WO | WO 92/14423 | 9/1992 |
| WO | WO 95/31945 | 11/1995 |
| WO | WO 96/03092 | 2/1996 |
| WO | WO 97/00054 | 1/1997 |
| WO | WO 00/30523 | 6/2000 |
| WO | WO 00/44319 | 8/2000 |
| WO | WO 00/44321 | 8/2000 |
| WO | WO 01/32099 | 5/2001 |
| WO | WO 01/78625 | 10/2001 |
| WO | WO 01/95838 | 12/2001 |
| WO | WO 02/13700 | 2/2002 |
| WO | WO 02/32347 | 4/2002 |
| WO | WO 03/003943 | 1/2003 |
| WO | WO 03/003951 | 1/2003 |
| WO | WO 2005/062900 | 7/2005 |
| WO | WO 2005/096975 | 10/2005 |
| WO | WO 2005/120400 | 12/2005 |
| WO | WO 2006/023514 | 3/2006 |
| WO | WO 2006/023671 | 3/2006 |
| WO | WO 2006/026425 | 3/2006 |
| WO | WO 2006/028971 | 3/2006 |
| WO | WO 2006/034396 | 3/2006 |
| WO | WO 2006/034436 | 3/2006 |
| WO | WO 2006/037013 | 4/2006 |
| WO | WO 2006/042334 | 4/2006 |
| WO | WO 2006/050500 | 5/2006 |
| WO | WO 2006/060420 | 6/2006 |
| WO | WO 2006/072941 | 7/2006 |
| WO | WO 2006/076712 | 7/2006 |
| WO | WO 2006/086241 | 8/2006 |
| WO | WO 2006/096167 | 9/2006 |
| WO | WO 2006/116761 | 11/2006 |
| WO | WO 2006/132945 | 12/2006 |
| WO | WO 2007/009107 | 1/2007 |
| WO | WO 2007/009123 | 1/2007 |
| WO | WO 2007/016368 | 2/2007 |
| WO | WO 2007/038611 | 4/2007 |
| WO | WO 2007/041698 | 4/2007 |
| WO | WO 2007/047098 | 4/2007 |
| WO | WO 2007/050322 | 5/2007 |
| WO | WO 2007/056433 | 5/2007 |
| WO | WO 2007/062080 | 5/2007 |
| WO | WO 2007/075411 | 7/2007 |
| WO | WO 2007/079021 | 7/2007 |
| WO | WO 2007/084257 | 7/2007 |
| WO | WO 2007/084268 | 7/2007 |
| WO | WO 2007/084810 | 7/2007 |
| WO | WO 2007/100591 | 9/2007 |
| WO | WO 2007/123920 | 11/2007 |
| WO | WO 2007/124130 | 11/2007 |
| WO | WO 2007/126622 | 11/2007 |
| WO | WO 2007/130699 | 11/2007 |
| WO | WO 2007/131026 | 11/2007 |
| WO | WO 2007/133608 | 11/2007 |
| WO | WO 2007/140382 | 12/2007 |
| WO | WO 2008/005627 | 1/2008 |
| WO | WO 2008/016598 | 2/2008 |
| WO | WO 2008/070863 | 8/2008 |
| WO | WO 2009/114381 | 9/2009 |
| WO | WO 2009130824 A1 * | 10/2009 |
| WO | WO 2012/027490 | 3/2012 |

OTHER PUBLICATIONS

Pyo, R. et al., "Targeted Gene Disruption of Matrix Metalloproteinase-9 (Gelatinase B) Suppresses Development of Experimental Abdominal Aortic Aneurysms," *J. Clinical Investigation*, 105(11):1641-1649, Jun. 2000.

Tambiah, J. et al., "Provocation of Experimental Aortic Inflammation Mediators and *Chlamydia pneumoniae*," *Brit., J. Surgery*, 88(7):935-940, Feb. 2001.

(56) References Cited

OTHER PUBLICATIONS

Walton, L.J. et al., "Inhibition of Prostoglandin E2 Synthesis in Abdonminal Aortic Aneurysms," *Circulation*, 48-54, Jul. 6, 1999.

Xu. Q. at al., "Sp1 Increases Expression of Cyclooxygenase-2 in Hypoxic Vascular Endothelium," *J. Biological Chemistry*, 275(32)24583-24589, Aug. 2000.

Choi, G. et al., "Percutaneous Endoscopic Lumbar Discemtomy by Transiliac Approach," *Spine*, 34(12):E443-446, May 20, 2009.

Database WPI, Week 198004, Thomson Scientific, London, GB; AN 1980-A8866C, XP002690114, -& SU 662 082 A1 (Tartus Univ) May 15, 1979, abstract, figures 1,2.

\* cited by examiner

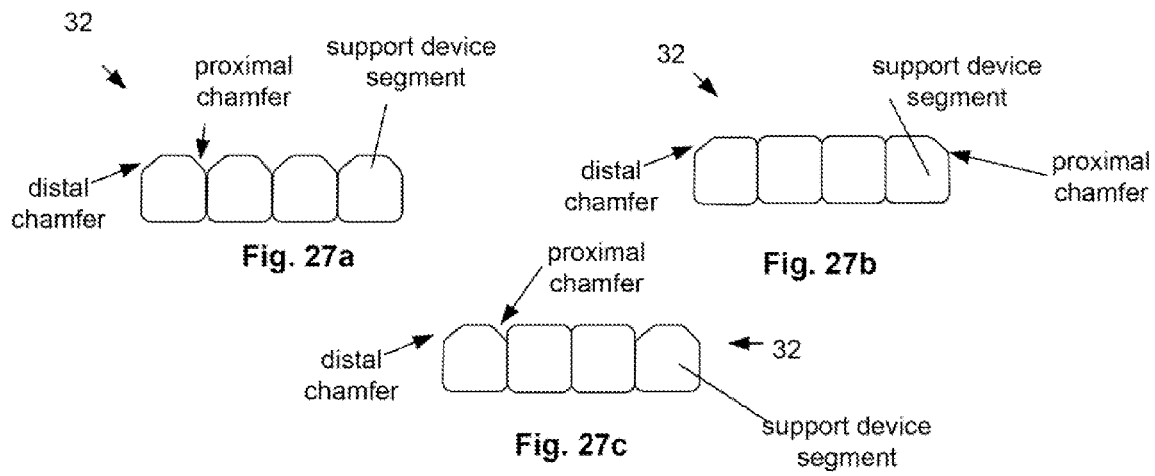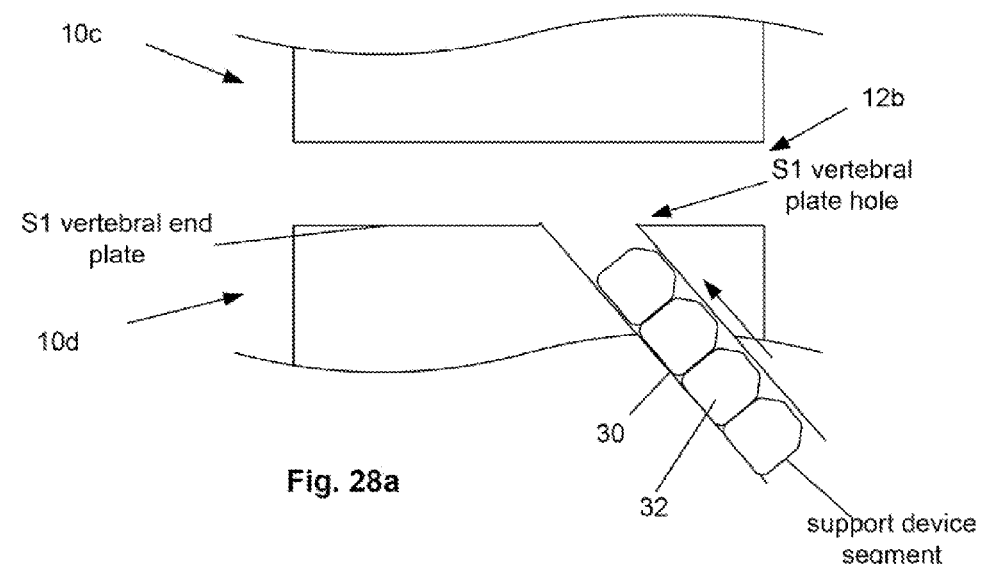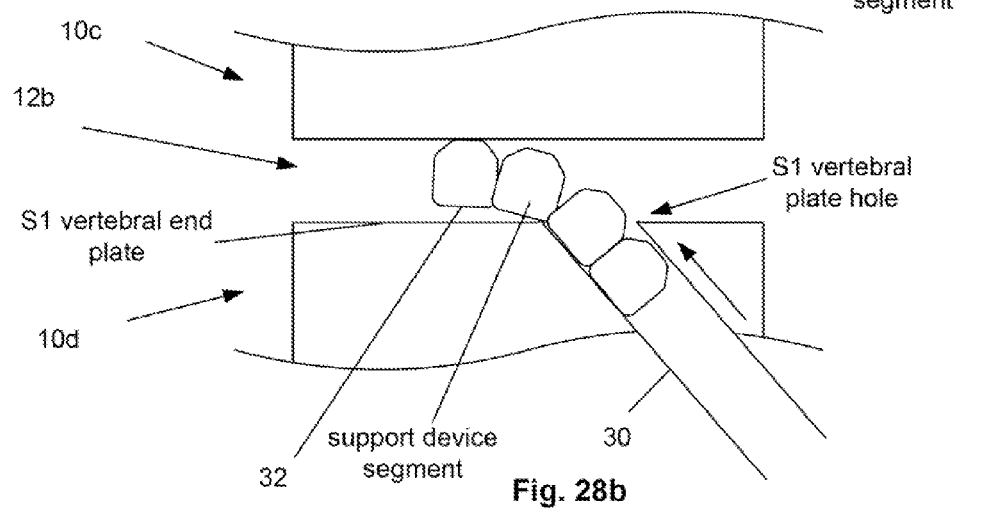

GUIDANCE TOOL AND METHOD FOR USE

CROSS-REFERENCE TO RELATED APPLICATIONS

This application claims priority to U.S. Provisional Application No. 61/456,806 filed 12 Nov. 2010, which is incorporated by reference in its entirety.

BACKGROUND OF THE INVENTION

1. Field of the Invention

A device, such as a flexible spinal fusion cage, which can articulate or bend in such a way that it will be able to be implanted through bone (i.e., in a trans-osseous path, through bone, such as the Ilium and/or sacrum joint approach into L5-S1 is disclosed.

2. Description of the Related Art

Typical lateral approach fusion implants (e.g., Nuvasive XLIF, Medtronic DLIF) are not able to implant into some orthopedic target sites for a variety of reasons.

Boney obstacles can impair access. FIGS. 1a and 1b illustrates the challenge of gaining lateral access to L4-L5 and L5-S1. The lower spine is shown, including the L3, L4, L5 and S1 vertebra (or Sacrum) 10a, 10b, 10c and 10d, and the L4-L5 intervertebral disc space 12a, L5-S1 intervertebral disc space 12b, and the Ilium or Iliac bone 14, the Sacral ala 16, the Sacroiliac joint 18, and the Symphysis pubis 20. Note the position of the Ilium relative to the direct lateral access pathway to the intervertebral disc spaces 12a and 12b. The Ilium 14 obstructs the target site for typical approaches to the respective disc spaces 12a and 12b.

Some doctors create large windows through the Ilium 14 to gain direct line of site access. This is a highly invasive approach removing a significant portion of bone, and requires significant surgical skill. Because of the inflexibility of the typical implants, the windows must be large enough to fit the entire implant cross section.

FIGS. 3 and 4 illustrate that the approach angle of a tissue retractor relative to the location of the fusion site is an issue. FIGS. 3 and 4 illustrate typical L4-L5 and L5-S1 approach paths 22a and 22b, respectively, for delivering the support device to the L4-L5 and L5-S1 intervertebral disc spaces 12a and 12b. The L4-L5 and L5-S1 approach angles 24a and 24b, respectively, can be measured from the transverse plane. The tissue retractor used in lateral fusion surgery provide line of site access to the disc space requiring a fusion cage insertion, the retractor "holds" tissue out of the way. They also create a working channel to pass tools through, they protect neural tissue, and they anchor to the superior and inferior vertebral bodies relative the disk space requiring fusion. Anything below the dashed line is very hard if not impossible to reach with direct lateral approach due to the Ilium. Even if the retractors are tilted as shown by the dotted line, the ability to insert an implant that is the length of the end plates of the VB's L4-L5 would be very difficult.

Furthermore, with the retractor positioned in the plane/direction as shown by the purple arrows above, the angle formed between the arrow tip and the VB's end plates would make inserting a monolithic fusion cage virtually impossible. A close up of this is shown below. A typical lateral fusion cage (gold) is the width of the end plate (a shown by the dotted lines) by the height if the disk (as shown by the parallel horizontal lines). The stiff, monolithic implant can be difficult if not impossible to turn around the corner at the lateral and/or anterior edge of the L5-S1 intervertebral space, as shown (as the bold circular dot) in FIG. 5.

Typical treatments for L5-S1 include anterior approaches, through the belly, TLIF (transforaminal lumbar interbody fusion), and PLIF (Posterior lumbar interbody fusion). Anterior and TLIF approaches are the most used. Both approaches are typically invasive.

SUMMARY OF THE INVENTION

Support or fixation devices and methods for access, controlling (steering) implants, and modifying implants are disclosed.

The device can be an implantable fixation device, such as a flexible fusion cage. The device can articulate and/or bend so the device can be delivered through a channel in one or more bones and into the L5-S1 intervertebral space, as shown in FIG. 6. The implant can articulate and be steered. For example, the implant can have hinges and/or be flexible.

A stand-alone fusion system and method is disclosed that can include deploying the support device with the transosseous delivery approach and optionally deploying screws and using targeting fixtures.

SUMMARY OF THE INVENTION

FIGS. 27a through 27c illustrate variations of the support device.

FIGS. 28a through 28d illustrate a variation of a method for delivering a variation of the support device through the bone channel, into the intervertebral space, and filling the bone channel.

DETAILED DESCRIPTION

Implantable orthopedic support devices and methods for implanting the same that can provide surgeons access, control (i.e., steering, translation) and implant into the L5-S1 disc space are disclosed. The method can deliver the device traveling through a tunnel drilled through the Sacroiliac joint into the L5-S1 joint space. The delivery method can be performed without disrupting nerves and major blood vessels. The implant has additional hardware to "lock" or stabilize the implant and the connect L5 to S1.

The support device can be one or more flexible fusion devices, such as unibody or multi-part cages or stents. The support devices can articulate and/or bend, for example to be able to make a sharp turn from exiting a transosseous bone channel and entering into the L5-S1 disc space. The support devices can have rigid sections connected by articulatable axes (e.g., hinges), or rigid sections and flexible lengths, or be flexible along the entire length of the device, or combinations thereof.

Figure 1A:
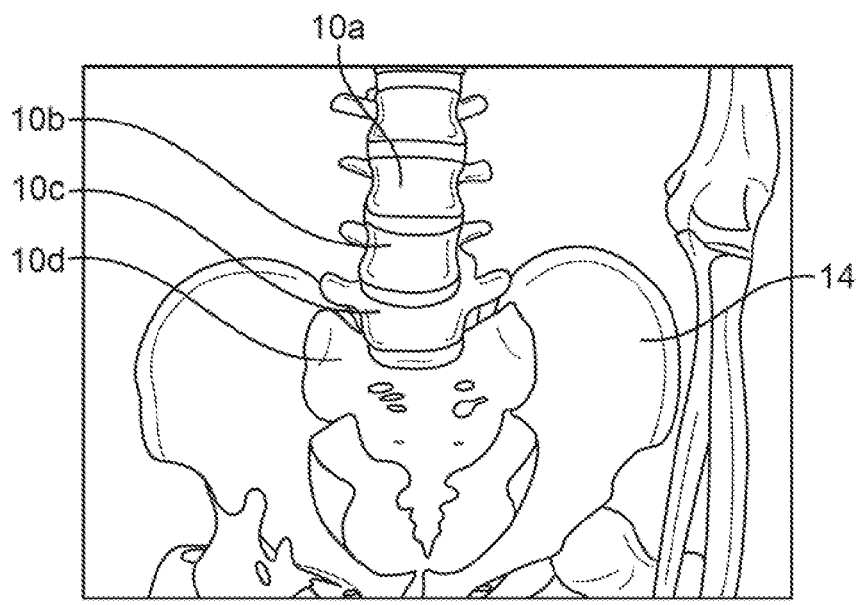
FIGS. 1a and 1b are direct anterior and anterior perspective views, respectively, of a variation of the lower lumbar spine.
Figure 1B:
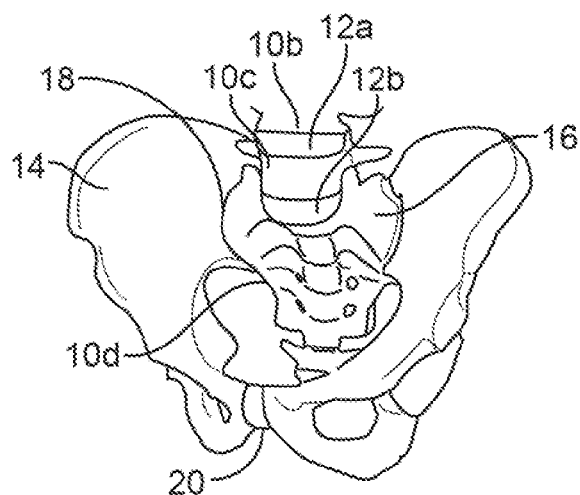
Figure 2:
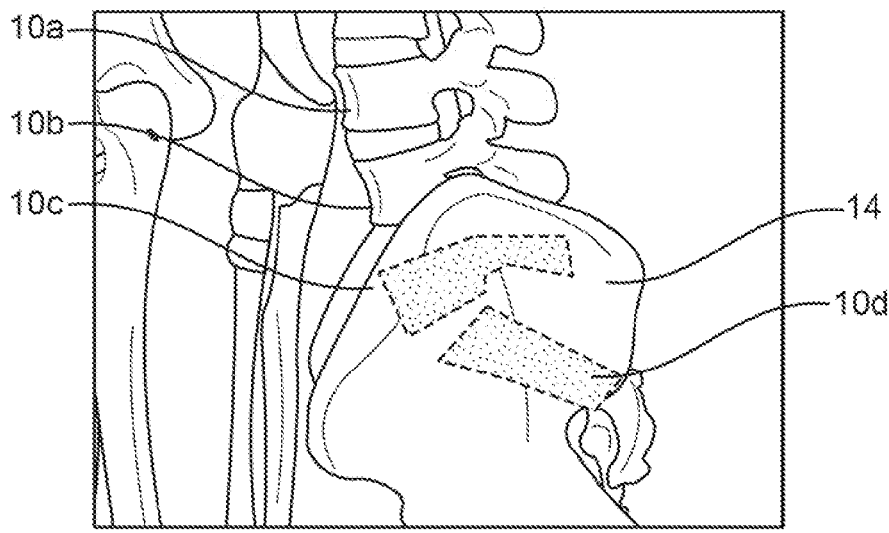
FIG. 2 is a lateral view of the lower lumbar spine with L5 and S1 shown in phantom views behind the Ilium.
Figure 3:
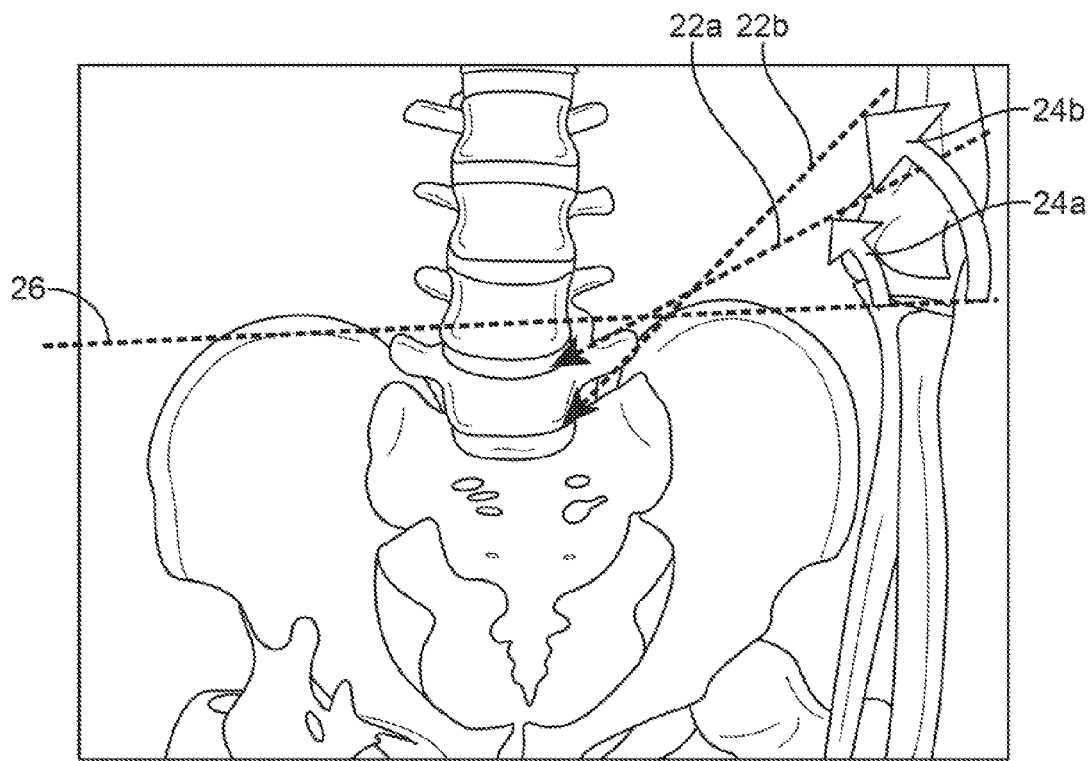
FIG. 3 is the view of the spine shown in FIG. 1 with L5-S1 and L4-L5 implant device delivery paths and approach angles.
Figure 4:
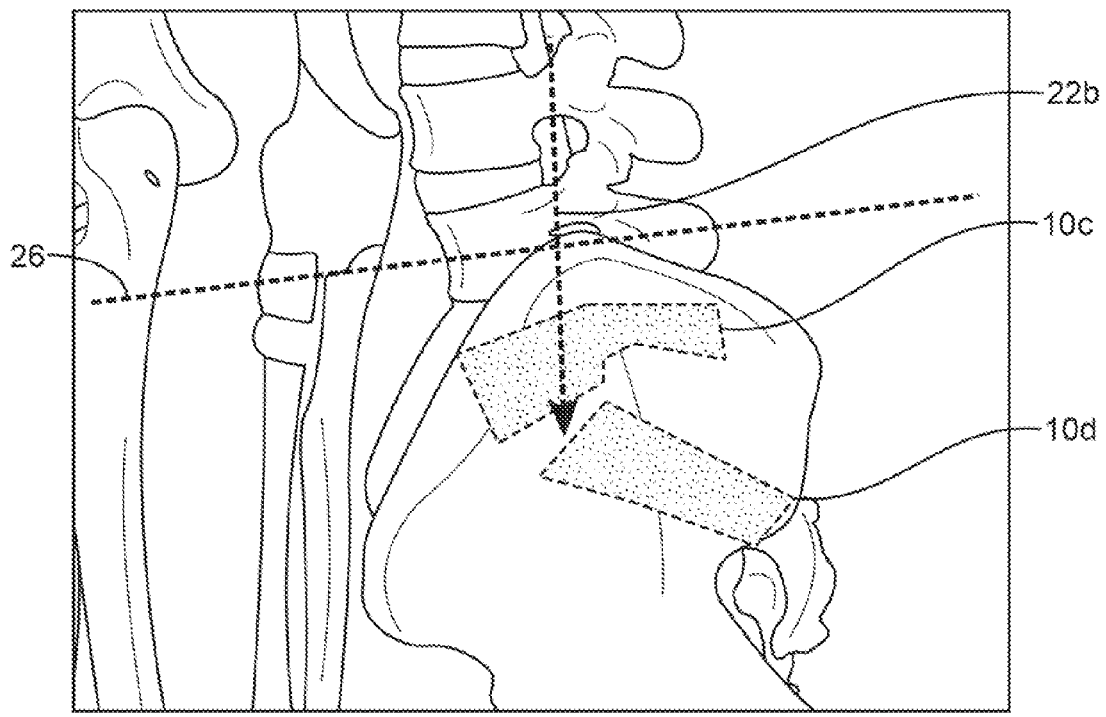
FIG. 4 is the view of the spine shown in FIG. 2 with the L5-S1 implant device delivery path and approach angle.
Figure 5:
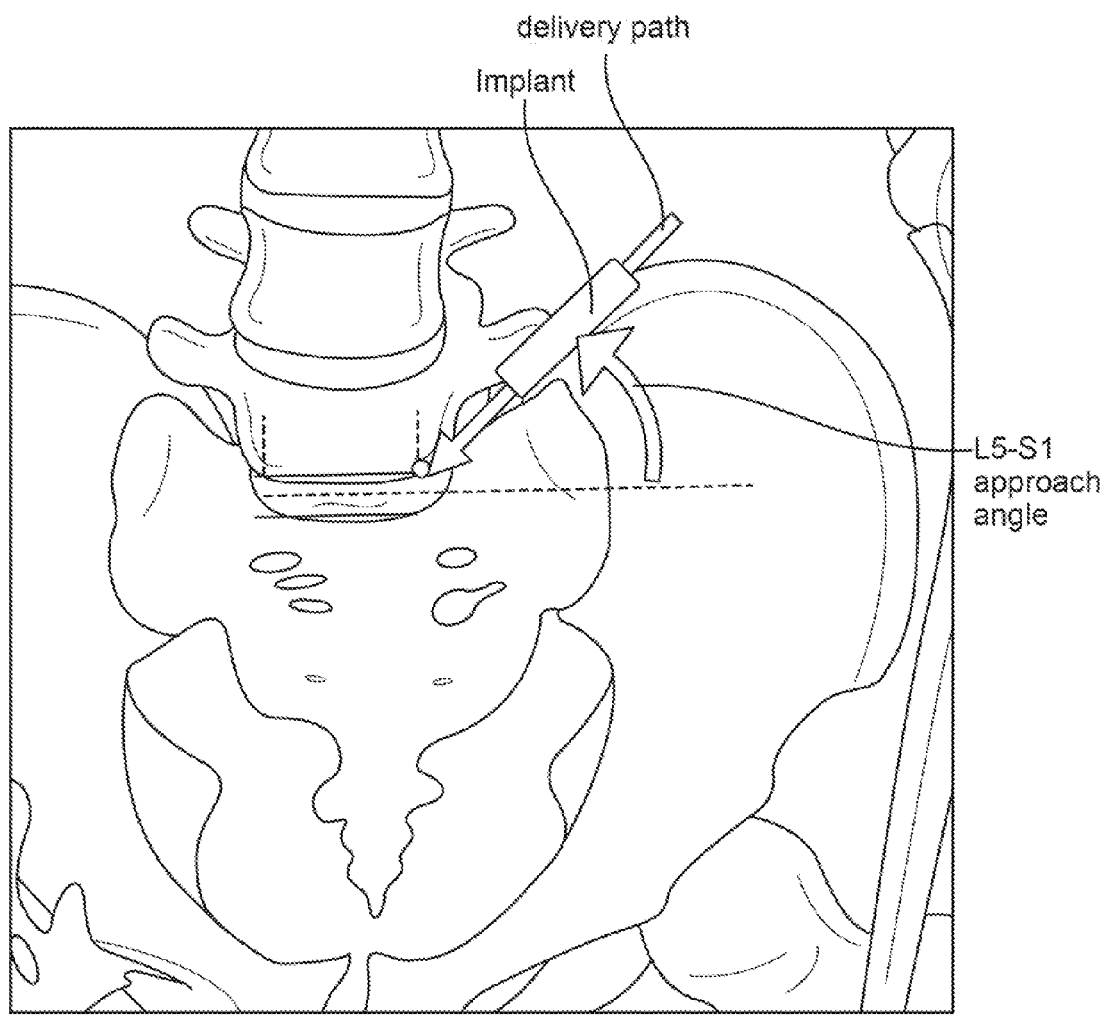
FIG. 5 is the view of the spine shown in FIG. 3 with L5-S1 implant device shown being inserted along a delivery path at an approach angle.
Figure 6:
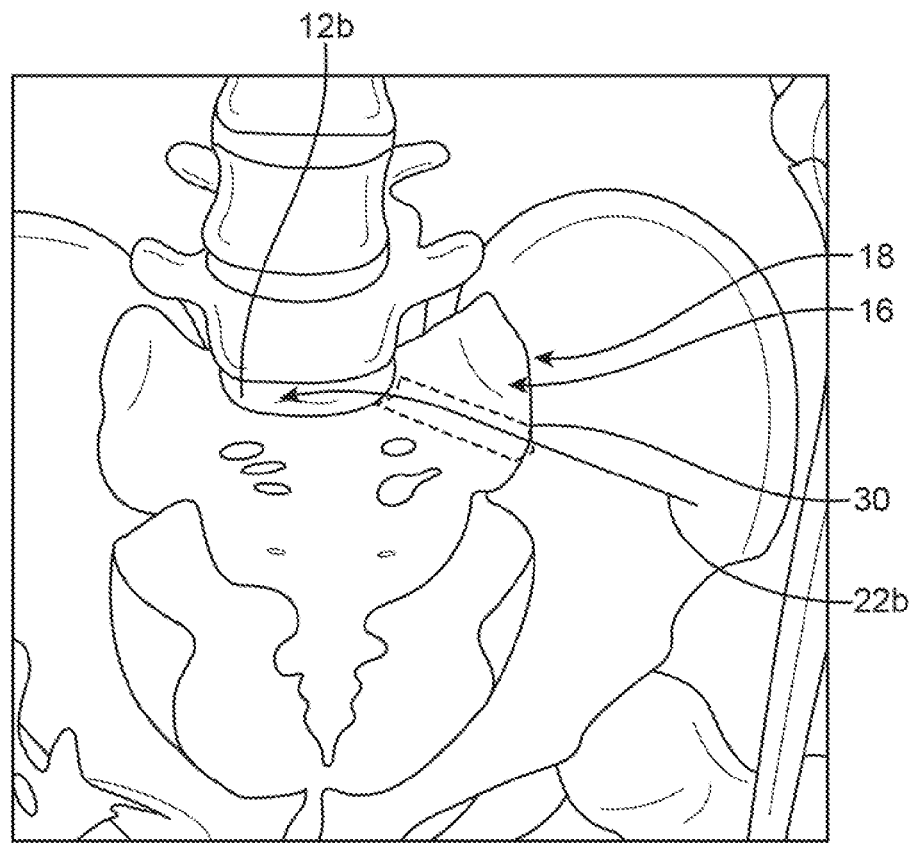
FIGS. 6 and 7 are anterior and lateral views, respectively, of a variation of a delivery path for an implant device through the sacrum.
Figure 7:
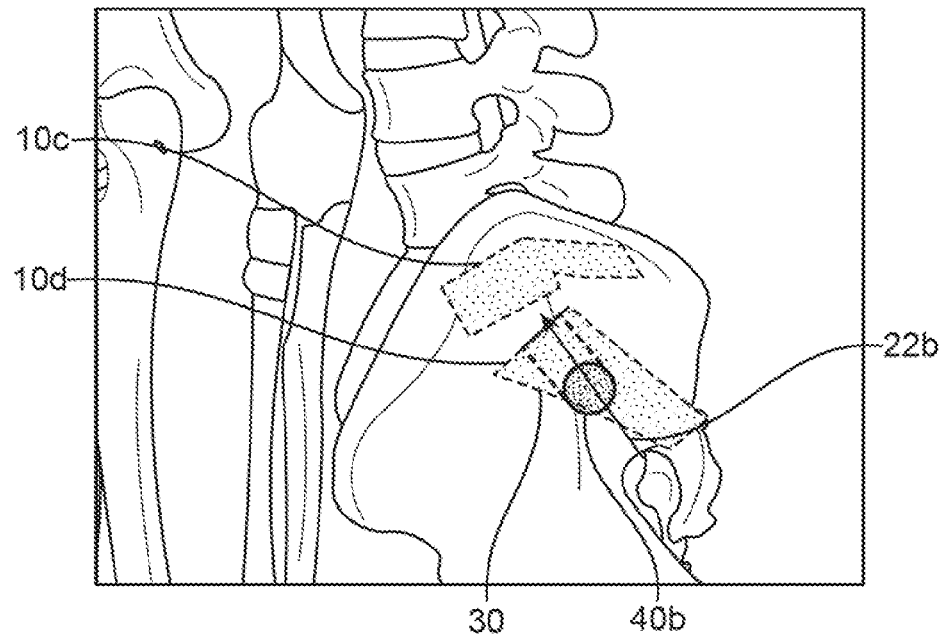

FIGS. 6 and 7 illustrate a transosseous access bone channel 30, as shown with dashed (i.e., phantom) lines, to the L5-S1 disc space 12b through the Ala 16 of the sacrum. The bone channel 30 can be drilled through the Ilium and/or sacrum, for example having a lateral port or opening on the lateral side of the Iliam, as shown in FIG. 7. The bone channel 30 can pass through the Sacroiliac joint 18. The bone channel 30 can be drilled with a straight and/or flexible or articulatable drill. The bone channel 30 can be hollow.

The bone channel 30 can be fitted with a collar or tube in contact with the perimeter of the channel. The collar or tube can be attached to a trocar. The tube can be delivered into the channel separate from a trocar. The tube can be hollow. The tube can have one, two, three or more lumens. The implant device can be inserted through the tube. The tube lumen(s) can have a low friction internal surface. For example, the internal surface can be coated with PTFE (e.g., Teflon).

FIG. 7 illustrates a lateral view of the lower spine. The transosseous access bone channel 30 can be oblique and non-perpendicular to the spine. Hence, the delivery (i.e., access) path 22 to the L4-L5 or L5-S1 disc space 12a or 12b can be oblique and non-perpendicular. The transosseous delivery path 22 can be through bone (e.g., through the Ilium and sacrum). The delivery path 22 can bypass all or major arteries, veins, muscles, nerves or combinations thereof. The delivery path 22 can pass through soft tissue, including skin fat and muscle, lateral to the Ilium 14.

Access tools, such as elongated retractors that can be fit through the move soft tissue out of the way to create the channel 30. The distal end of the implanted support device 32 can be atraumatic, but come to a rounded tip to spread or dissect tissue away from the delivery path 22 during translation of the device 32 during delivery.

One or more deployment tools can delivery and deploy the support device 32. The deployment tools can allow the support device 32 to passively articulate or flex in response to resistive forces from surrounding tissue and/or actively articulate or flex the support device upon control inputs (e.g., pushing, twisting, button pressing, level manipulation, etc.) from the user. The interface or connection between the deployment tool and the support device 32 can bend, flex, steer, or a combination thereof. The deployment tool or tools can clear out the disk space 12 (i.e., performing a partial or complete discectomy). The deployment tools can articulate and/or flex and follow the delivery paths shown for the support device herein, for example to reach the L4-L5 and/or L5-S1 disc space 12a and/or 12b. The deployment tools can be pre-angled to reach and remove disk material, for example the deployment tool can be rigid and bent or flex.

A stand alone fusion system and method can include utilizing the support device in a transosseous approach optionally with additional securing and/or targeting devices.

Figure 8A:
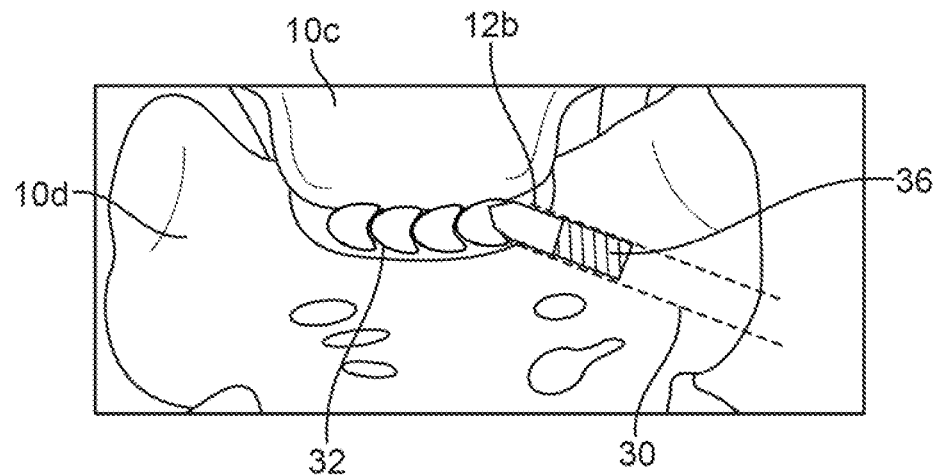
FIGS. 8a and 8b illustrate variations of and a delivery method for the implant support device.

FIGS. 8a through 9 illustrate that additional securing devices 34 and methods can be used to fix, stabilize, help heal, minimize or prevent migration of the support device 32, reduce bone (e.g., L4, L5, S1, and combinations thereof) movement relative to the support device 32 and relative to the other bones, and combinations thereof. The supplement stabilization elements or securing devices 34 can secure the position of the flexible implant to the surrounding bone. The support device 32 can completely fuse to the ends plates of the surrounding bone (e.g., L4, L5, S1, and combinations thereof). Other securing devices 34 can be used in combination with the support device 32 such as facet fusion elements, pedicle-based screws and rods, anterior plates, and combinations thereof.

FIG. 8a illustrates that the support device 32 can be long enough and/or inserted at a length into the disc space 12 so that a portion of the support device 32 extends into the bone channel 30 after the insertion is complete. The portion of the support device 32 inside of the bone channel 30 can be straight or at an angle to the portion of the support device 32 directly adjacent and on the outside of the bone channel 30. For example, the support device 32 can be flexible through the distal ⅔ of the length of the support device 32 and the proximal ⅓ of the length of the support device 32 can be rigid or not flexible, but articulatable with the distal ⅔ of the length of the support device 32. The proximal ⅓ of the length of the support device 32 can remain within the sacrum access tunnel or bone channel 30 after the support device 32 is positioned at the target site in the disc space 12. The stiff proximal section 36 of the support device 32 can be hingedly and/or flexibly connected to the distal length of the support device 32. The support device 32 can be fixed to the bone channel 30, for example at the proximal length 36 of the support device 32. The proximal end 36 of the support device 32 can be glued, impacted, screwed, or a combination thereof, to the bone channel 30 and/or to a collar in the bone channel 30. The support device proximal rigid end 36 can be made from any material listed herein including PEEK, allograft, Ti, PE, PMMA, milled bone, steel, or combinations thereof.

The proximal and/or distal ends of the support device 32 can have a porous bone ingrowth matrix on the outer surfaces of the support device 32, for example promoting bone growth into the support device fixing the support device to surrounding bone (e.g., in the bone channel and/or L4, L5, and/or S1). The proximal, distal or entire length of the support device can be hollow, cannulated, threaded, have teeth, be expandable, barbed, be multiple pieces, or combinations thereof (e.g., to promote bone growth into the support device).

Figure 8B:
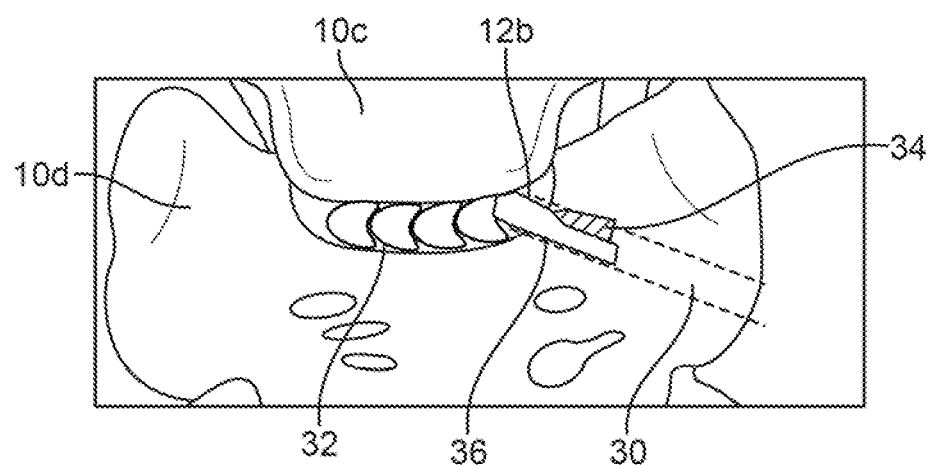

FIG. 8b illustrates that an interference screw 34 can anchor the stiff or flexible proximal section 36 of the support device 32. The interference screw 34 can be inserted between the proximal length 36 of the support device 32 and the bone channel 30 and/or between the distal length of the support device 32 and the adjacent bone 10. The interference screw 34 can pressure-fit the support device 32 against the bone channel 30 and/or adjacent bone 10. The interference screw 34 can be inserted parallel with the longitudinal axis of the length of the support device 32 adjacent to the interference screw 34. The interference screw 34 can be made from any material listed herein including PEEK, allograft, Ti, PE, PMMA, milled bone, steel, or combinations thereof.

Figure 9A:
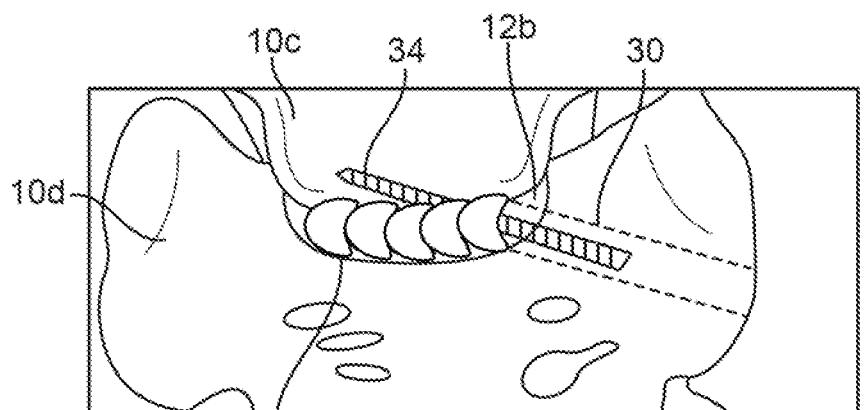
FIGS. 9a through 9c illustrate a variation of the implant support device and variations of delivery methods.
Figure 9B:
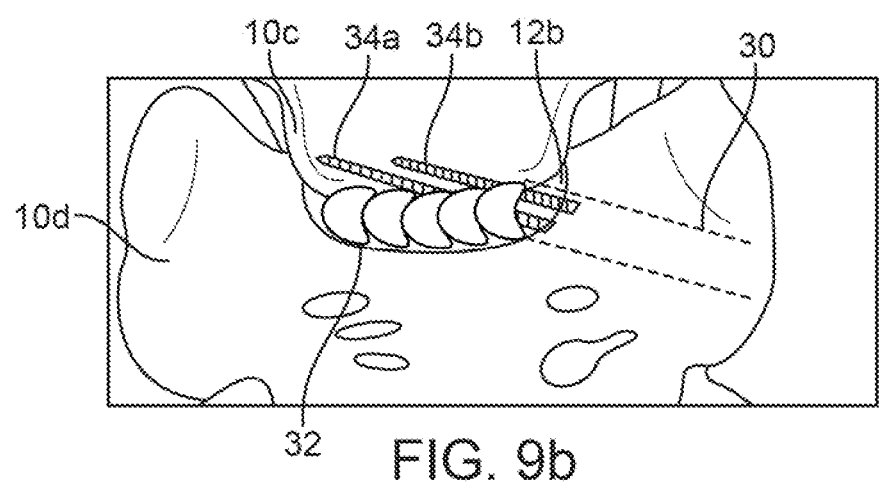
Figure 9C:
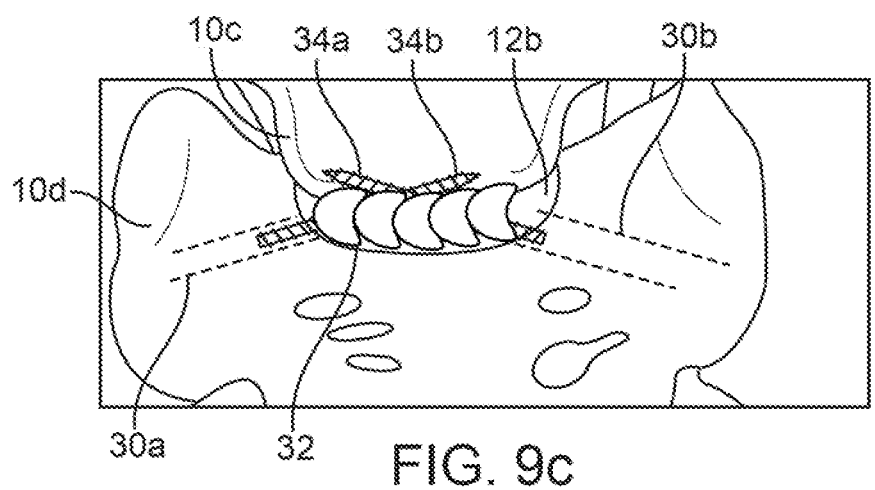

FIGS. 9a through 9c illustrate that the support device can have additional transosseous single, double, or crossing lag screws, bolts, spears, tacks, or other anchors or securing devices (referred to as "screws") 34 inserted through or around the support device 32 and into surrounding bone 10 and/or soft tissue. The screws 34 can pass through the support device 32 or outside the support device 32 in front, back and/or to the side of the support device 32 (i.e., anteriorly, posteriorly and/or laterally).

The outer diameter of the screws 34 can be larger, smaller or the same as the inner diameter of the bone channel (or tube lumen) through which the respective screw 34 is to be delivered. The proximal ends of the screws 34 can be threaded or smooth. The proximal end of the screws 34 can be can be inside a larger diameter plug smaller than, equal to or larger than the bone channel or tube lumen inner diameter. The screws 34 can be rigid.

FIG. 9a illustrates that a single screw 34 can be inserted through a bone channel 30. FIG. 9b illustrates that a first screw 34a and a second screw 34b can be inserted through a bone channel 30. FIG. 9c illustrates that a first screw 34a can be inserted through a first bone channel 30a and a second screw 34b can be inserted through a second bone channel 34b. The first bone channel 30a can be on the same or opposite side of the target site from the second bone channel 30b.

Figure 10:
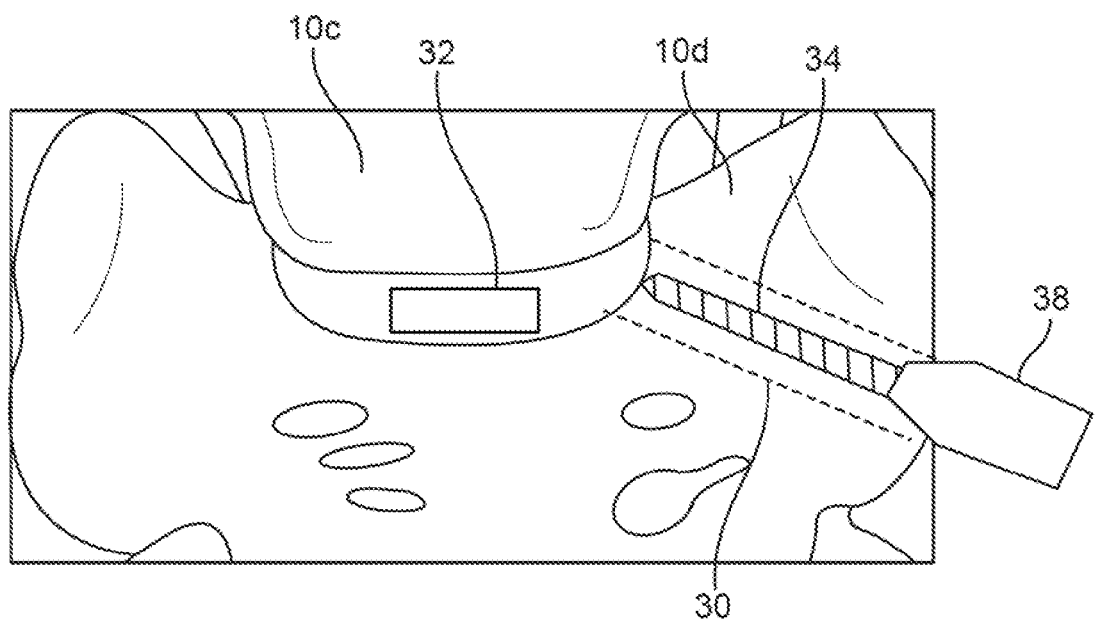
FIG. 10 illustrates a variation of a plug and a method for delivering the plug into the delivery channel through bone.

FIG. 10 illustrates that a blocking plug 38 can be inserted into the bone channel 30 and/or tube lumen. The plug 38 can have an outer diameter smaller than, equal to or larger than the inner diameter of the bone channel 30 and/or tube lumen. The plug 38 can taper to a smaller diameter on the distal end of the plug 38. The plug 38 can be fixed to the screw 34. The plug 38 can be surrounded by bone cement and/or an adhesive. The plug 38 can be used to center the screw 34. The plug 38 can interference fit with the bone channel 30, for example preventing and/or minimizing migration of the support device 32 and/or screw 34. The plug 38 and/or screw 34 can penetrate or not penetrate the support device 32. The plug 38' and/or screw 34 can make contact with (e.g., interference fit or bump up against) the support device 32, for example to hold or brace the support device 32 in a deployed position (e.g., expanded, properly articulated, and/or located). The plug 38 can be inserted to a depth to push on the proximal end 36 of the support device 32 (e.g., to position the support device). The plug 38 can be positioned behind the support device 32 (e.g., posterior spine), pushing the support device 32 forward (e.g., distally or anteriorly) and blocking the access pathway (e.g., bone channel 30). The blocking plug can seat against and/or block lateral channel port.

Figure 11A:
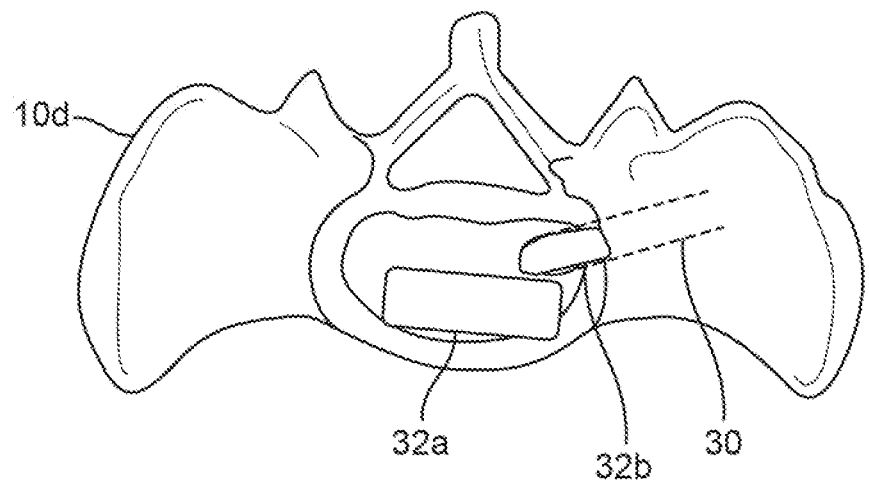
FIGS. 11a and 11b are superior views of the sacrum and variations Of methods for deploying multiple implant devices.
Figure 11B:
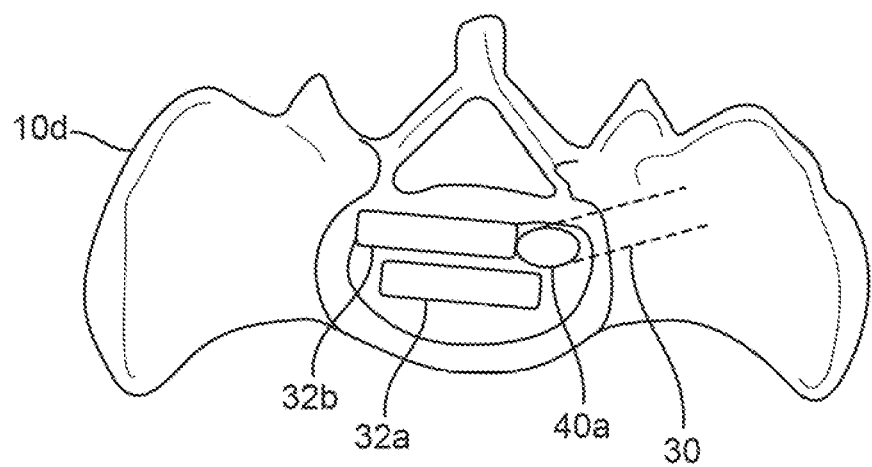

FIGS. 11a and 11b illustrate that first and second support devices 32a and 32b can be inserted into the target site. The first support device 32a can be anterior or posterior, lateral or medial, superior or inferior (e.g., in contact or in different disc spaces such as a first support device 32a in the L4-L5 space 12a and the second support device 32b in the L5-S1 space 12b), or a combination thereof of the second support device 32b. For example, different diameter support devices 32 can be inserted through different diameter bone channels 30 and/or tube lumens (e.g., larger diameter support devices 32 can be inserted through larger diameter bone channels 30 and smaller diameter support devices 32 can be inserted through smaller bone channels 30).

Each bone channel 30 can have a medial bone channel port 40a and a lateral bone channel port 40b. The lateral bone channel port 40b can be on the lateral side of the Ilium. The medial bone channel port 40a can be at the bone face exposed to the target site, such as adjacent to and in fluid communication with the respective intervertebral disc space.

Figure 12A:
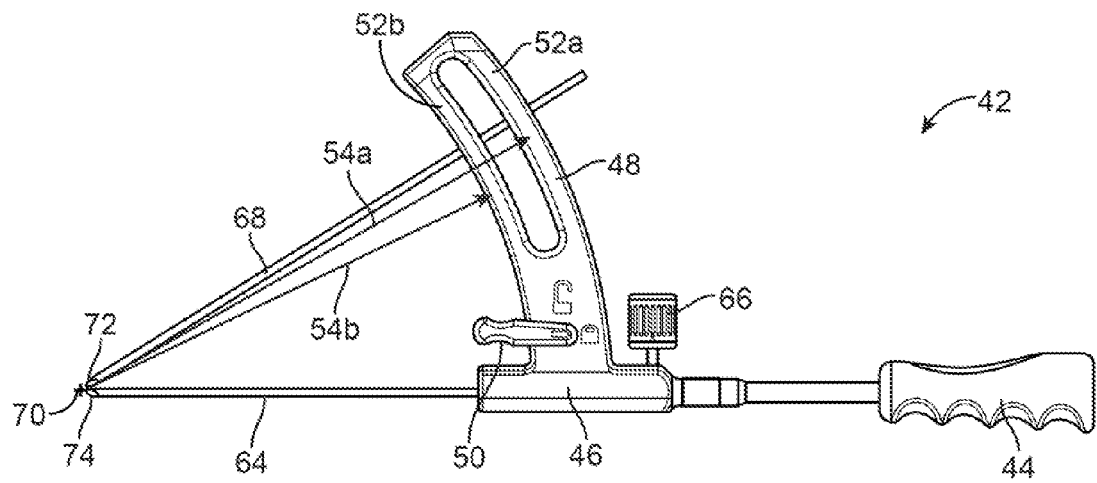
FIGS. 12a and 12b are side and side perspective views of a variation of a deployment tool for deploying support devices in the spine with a reamer wire and an anchor wire.
Figure 12B:
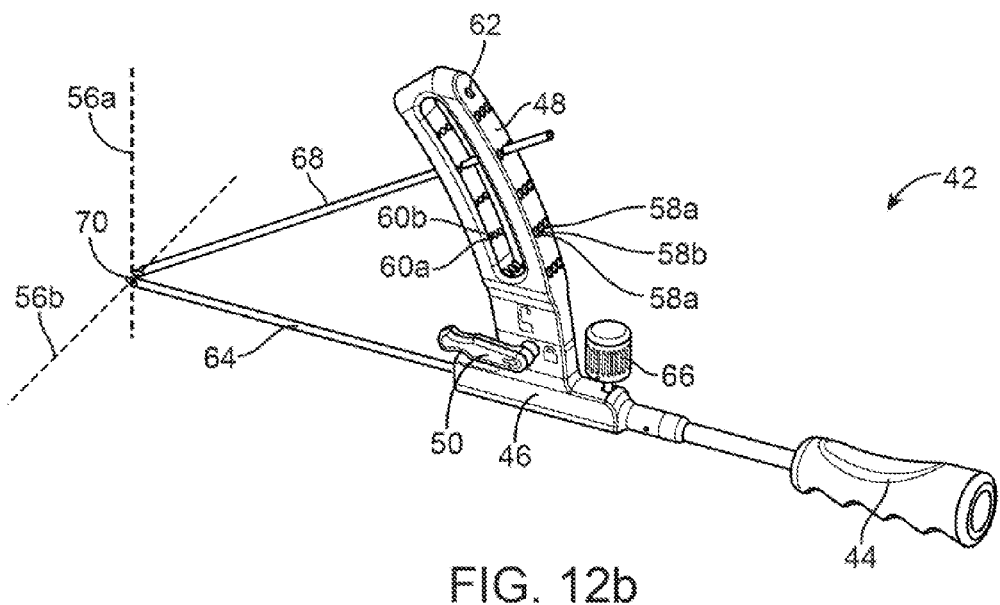

FIGS. 12a and 12b illustrate a guidance tool (i.e., guide tool) 42 that can be used to guide wires used to access the target site, such as the L5-S1 vertebral joint space 12b. The guide tool 42 can have a handle 44, a guide base 46, a wire holding fixture 48 or combinations thereof. The handle 44 can be releasably or fixedly attached to the guide base 46. The guide base 46 can be fixedly or releasably attached to the wire holding fixture 48. The guide base 46 can have a fixture lock 50 that can attach and release the wire holding fixture 48 to the guide base 46.

The wire holding fixture 48 can have an outer fixture 52a and an inner fixture 52b. The outer fixture 52a and the inner fixture 52b can have radii of curvature 54a and 54b, respectively, with respect to a target lateral axis 56a from about 4 in. to about 10 in., more narrowly from about 5.5 in. to about 7 in., for example about 5.5 in. or about 6 in., and radii of curvature with respect to a target vertical axis 56b from about 4 in. to having no curvature with respect to the target vertical axis 56b, more narrowly from about 4 in. to about 10 in., more narrowly from about 5.5 in. to about 7 in., for example about 5.5 in. or about 6 in. The outer and inner fixture radii of curvature about the target lateral axis can be the same or different as the radii of curvature about the target vertical axis.

The outer fixture 52a can be radially separated by a gap from the inner fixture 52b.

The outer fixture 52a and inner fixture 52b can have one or more reamer wire holes. The outer fixture 52a can have outer lateral reamer wire holes 58a and outer central reamer wire holes 58b. The inner fixture 52b can have inner lateral reamer wire holes 60a and inner central reamer wire holes 60b. Each central reamer wire hole can have a lateral reamer wire hole on one or both lateral sides of the central reamer wire hole, forming reamer wire hole rows. The outer reamer wire holes can align radially with the inner reamer wire holes.

The reamer wire hole rows can be spread apart by about 5° increments. The reamer wire holes can be replaced or used in addition to a reamer wire holder on a track that can be slid up and down the wire holding fixture (e.g., like a protractor), being adjustable, for example, in infinitely small increments within the range allowed by the fixture.

The wire holding fixture 48 can have a visualization pin hole 62, for example, at the terminal end of the wire holding fixture 48 away from the guide base 46. The visualization pin hole 62 can be configured to hold a pin substantially parallel to the anchor wire 64.

The anchor wire 64 can extend from the guide base 46 colinear or parallel to the handle 44. The anchor wire 64 can be releasably attached to the guide base 46. The guide base 46 can have an anchor lock 66 to releasably fix the anchor wire 64 to the guide base 46. A length of the anchor wire 64 can be slid into the guide base 46 before securing, locking or otherwise fixing the anchor wire 64 to the guide base 46.

The reamer wire 68 can slide through the desired reamer wire holes 58 and/or 60. The reamer wire 68 can be slidably received by the reamer wire holes 58 and/or 60. The reamer wire 68 can be cannulated.

The use of the word "wire" to describe the anchor wire 64, reamer wire 68 or other wires is exemplary only. The wires can be hollow or solid and can be rods, leaders, staffs, shafts, needles, trocars, pins, bars, cylinders, poles, bars, or combinations thereof. The wires can have cross-sections of circular, oval, square, triangular, rectangular shape, or combinations thereof. The anchor wire can have a diameter from about 1 mm to about 10 mm, more narrowly from about 3 mm to about 5 mm, for example about 3 mm or about 4 mm. The reamer wire can have a diameter from about 1 mm to about 10 mm, more narrowly from about 2 mm to about 4 mm, for example about 3 mm or about 4 mm.

The reamer wire 68 can extend to intersect and contact the anchor wire 64 at a guide target location 70. The reamer wire distal terminal tip 72 and the anchor wire distal terminal tip 74 can meet or touch or almost meet or touch at the guide target location 70. The guide target location 70 can be the origin location for the target lateral axis 56a and the target vertical axis 56b. The guide target location 70 can be placed in or adjacent to the desired target vertebral disc space 12 and/or the medial bone channel port 40a.

Figure 13A:
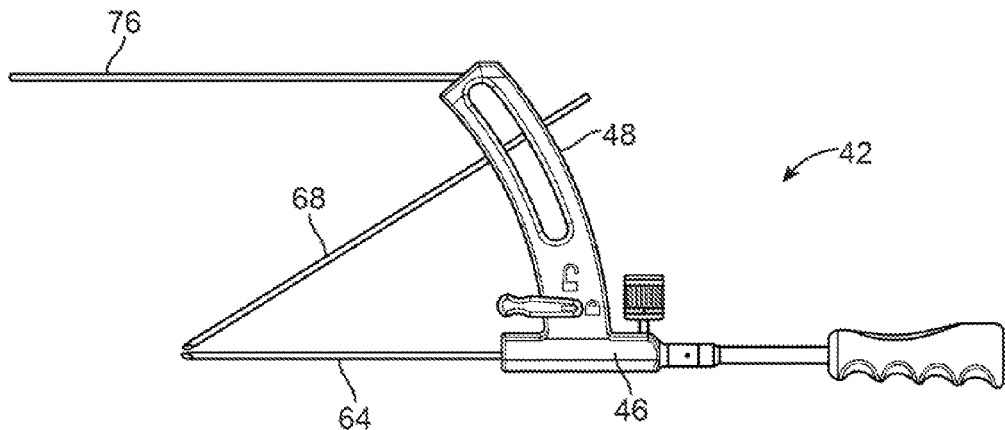
FIGS. 13a through 13c are side, side perspective, and rear perspective views of the tool in FIGS. 12a and 12b with an x-ray guidance pin.
Figure 13B:
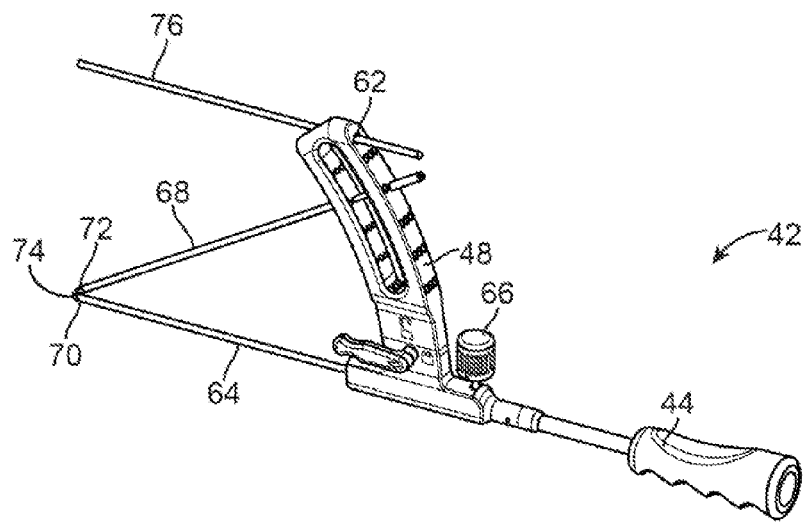
Figure 13C:
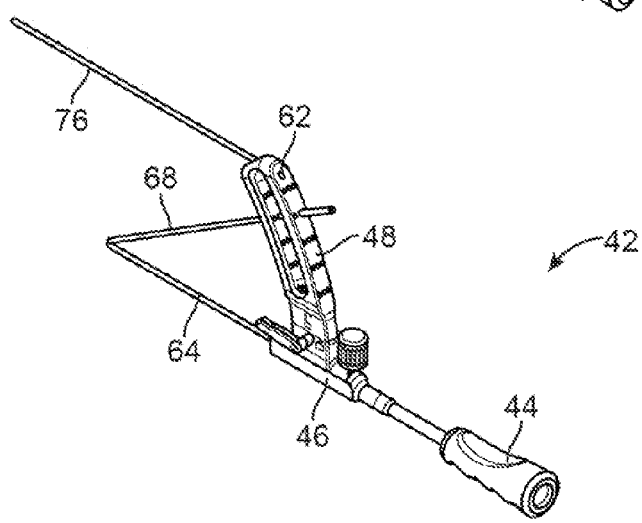

FIGS. 13a and 13b illustrate that a visualization guidance pin 76 can extend through the visualization pin hole. The visualization guidance pin can be parallel with the anchor wire. The visualization guidance pin 76, anchor wire 64 and reamer wire 66 can be co-planar with any combination or all of each other.

The visualization guidance pin 76 can be highly visible for a chosen visualization technique. For example, all or part of the visualization guidance pin 76 can be radiopaque, echogenic, radioactive, magnetic, fluorescing, electrically conductive or resistant, or combinations thereof. The visualization guidance pin can be configured to be observed with the naked eye, MRI, x-ray, CAT scanning, sonograms, fluoroscopy, or combinations thereof.

The guidance tool 42 can hold the guidance pin 76 at an orientation and position so the guidance pin 76 does or does not contact or pierce the patient.

The distal terminal end of the reamer wire can have a reamer wire tip 72. The distal terminal end of the anchor wire can have an anchor wire tip 74. The wire tips 72 and 74 can have chisel tip, bullet tip, needle tip and/or hollow tip configurations.

One or both of the wire tips 72 and/or 74 can have a visualization marking the same or different from the remainder of the respective wire. For example, the wire tips can be radiopaque whether or not the remainder of the wire is radiopaque. Similarly, the wire tips can be echogenic, magnetic, radioactive, fluorescing, electrically conductive or resistant, or combinations thereof.

Figure 14:
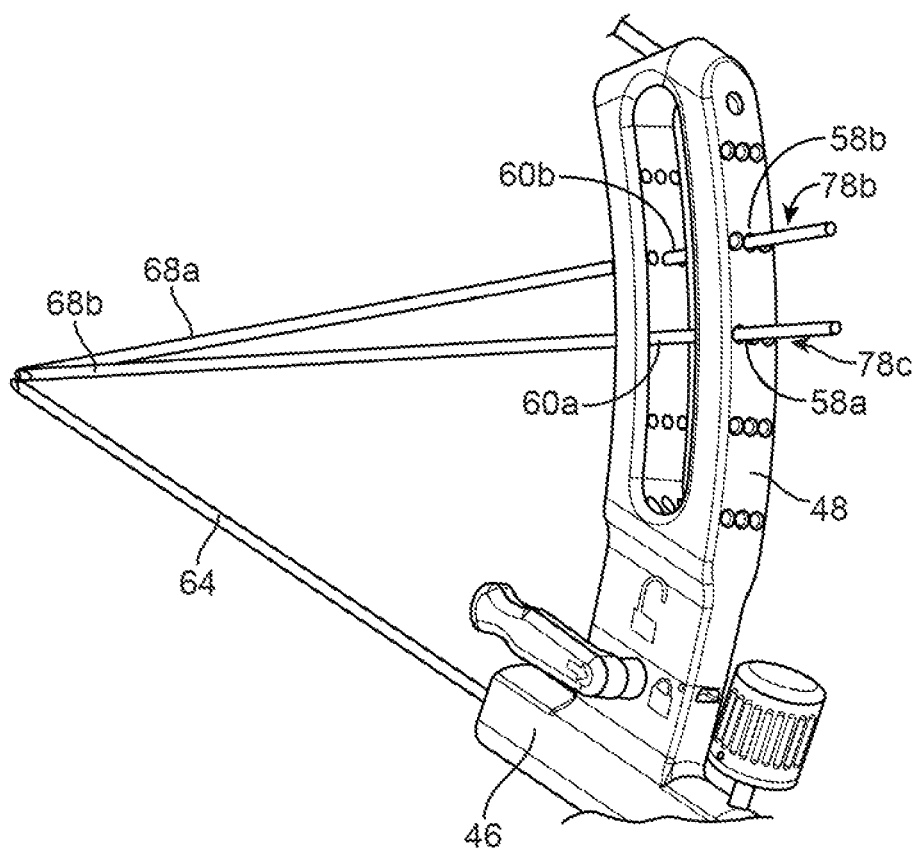
FIG. 14 is a close up view of a wire holding fixture of the tool of FIGS. 12a and 12b with a second reamer wire.

FIG. 14 illustrates that a first reamer wire 68a can be inserted through the outer and inner central reamer wire holes 58b and 60b in a second reamer wire hole row 78b (as enumerated from the terminal end of the wire holding fixture, although the enumeration is arbitrary and can start at either end). A second reamer wire 68b can be inserted through the outer and inner lateral reamer wire holes 58a and 60a in a third reamer wire hole row 78c. The first and second reamer wires 68a and 68b can be inserted concurrently or subsequently and can be withdraw concurrently or subsequently from the wire holding fixture 48. For example, if the user is not satisfied with the path of the first reamer wire 68a, the user can withdraw the first reamer wire 68a and re-insert the first reamer wire 68a through a different set of holes or insert a second reamer wire 68b through a different set of holes. Also for example, if the user wishes to create two access paths to the target site, the user can insert a first reamer wire 68a through a first set of holes and a second reamer wire 68b through a second set of holes.

Figure 15A:
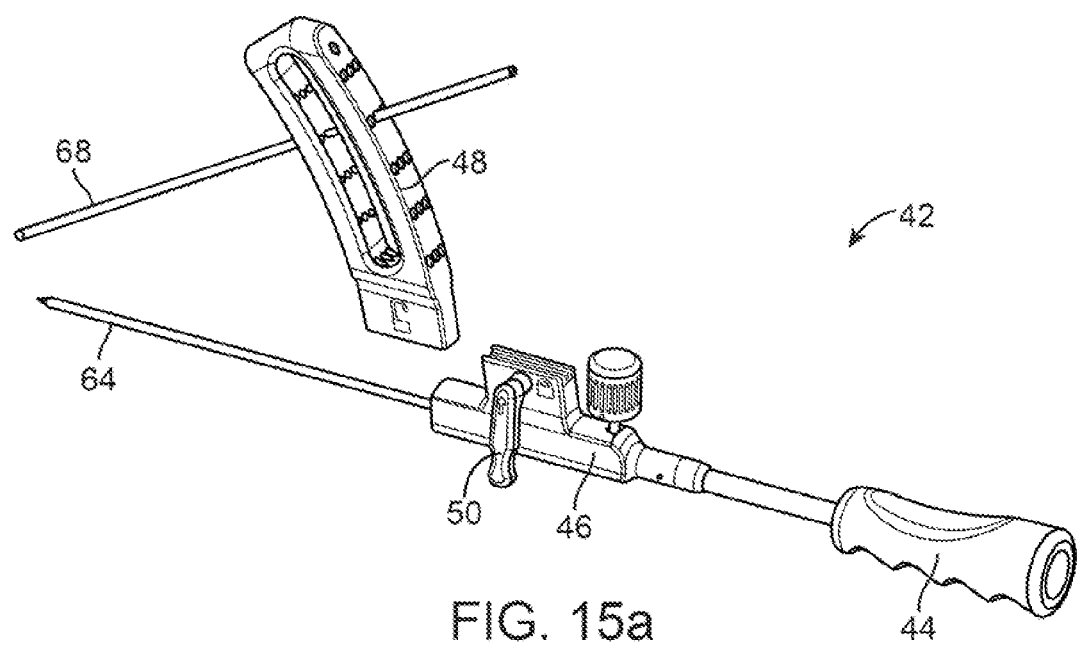
FIGS. 15a and 15b are side perspective and top perspective views, respectively, of the tool of FIGS. 12a and 12b in a partially disassembled configuration.
Figure 15B:
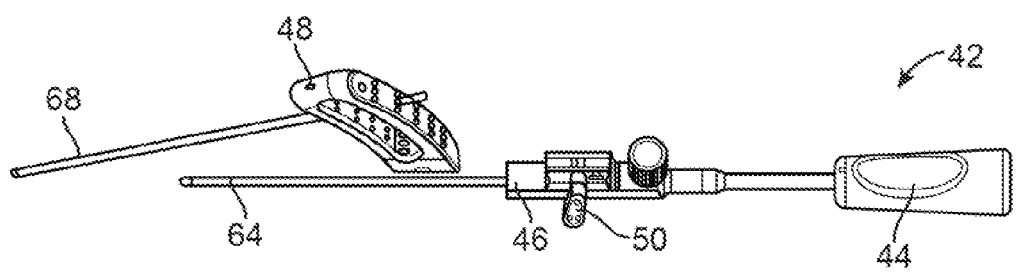
Figure 15C:
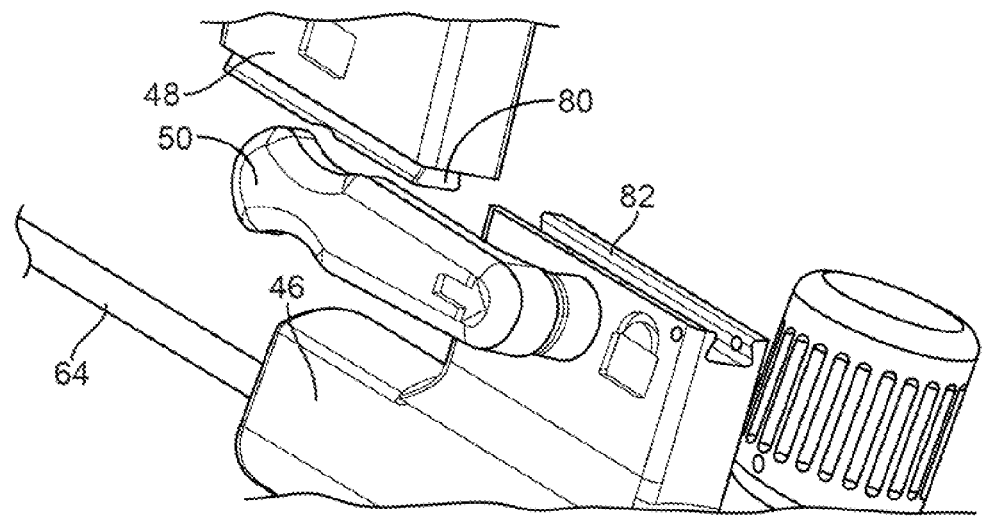
FIG. 15c is a close up view, of the tool of FIGS. 12a and 12b in a partially disassembled configuration.

FIGS. 15a through 15c illustrate that the guide tool 42 can be disassembled. For example, the wire holding fixture can be separated from and re-attached to the guide base. During use, after the reamer wire is in position with the reamer wire tip at the target site, the wire holding fixture can be separated from the guide base. The fixture lock can be turned to release the wire holding fixture from the guide base. The anchor wire can then be removed from the target site by pulling the handle and the wire holding fixture can be slid off the reamer wire, leaving only the reamer wire at the target site.

FIG. 15c illustrates that the wire holding fixture 48 can have a fixture interface 80, such as a tongue, and the guide base 46 can have a base interface 82 such as a groove. The fixture interface can releasably and slidably attach to the base interface. The fixture interface and the base interface can be configured to prevent or minimize separation of the wire holding fixture from the guide base in any direction other than parallel with the anchor wire.

Figure 16A:
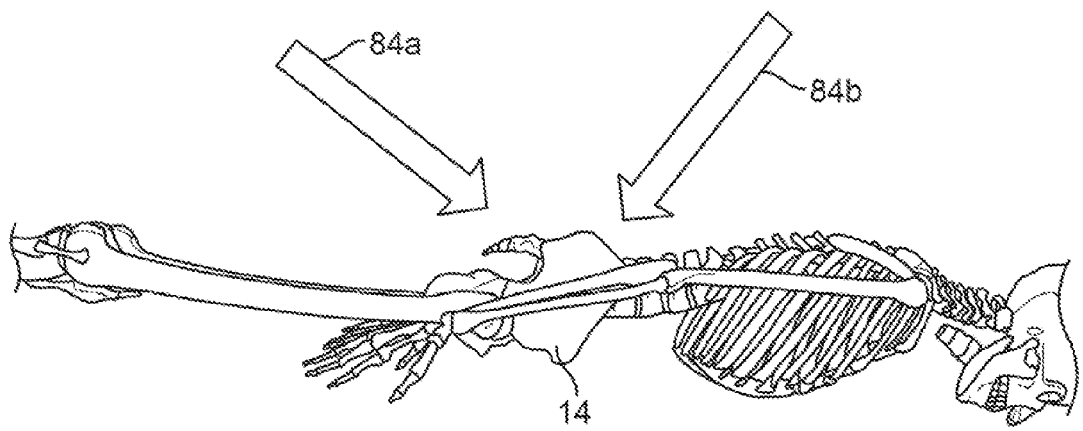
FIGS. 16a and 16b are a side view and a close-up side view, respectively, of a skeleton showing various visualization perspectives of a target site.
Figure 16B:
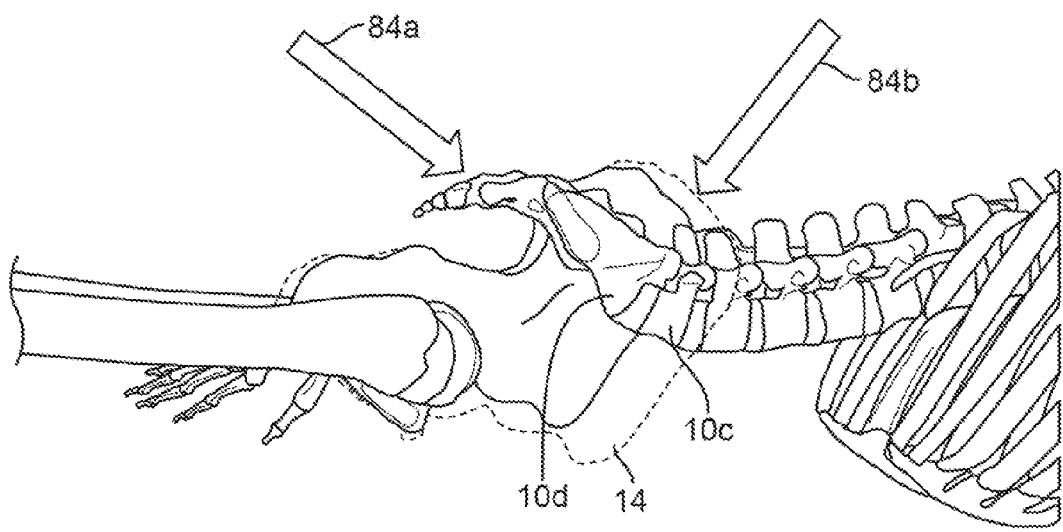

FIGS. 16a and 16b illustrate inlet views, perpendicular to the S1 end plate, shown by arrow 84a, and outlet view parallel to the S1 end plate, shown by arrow 84b, used for visualizing a target site of the L5-S1 vertebral joint. FIG. 16b shows the Ilium in partial see-through to illustrate the L5-S1 joint. The visualizations can be performed using a C-arm and fluoroscopy, MRI, CAT, x-rays, sonograms, or combinations thereof.

FIGS. 17a through 17g illustrate the initial anchor wire placement parallel to the S1 end plate, through the Ilium and sacroiliac joint, for example, performed with lateral view visualization (e.g., X-ray). The anchor wire 64 can be inserted along an anchor wire delivery path 86 through the Ilium. The anchor wire tip 74 can be inserted through the bone. The anchor wire tip 74 can be positioned in the S1 vertebra 10d inferior and adjacent to the S1 vertebral body endplate, as indicated by anchor wire target site position "x" 88 in FIG. 17b. The anchor wire can be guided by lateral fluoroscopy x-ray parallel to the S1 end plate. The anchor wire can be attached to the guide base or not attached to the guide base during the insertion of the anchor wire and placement of the anchor wire tip at the target site in the S1 vertebra.

Figure 17B:
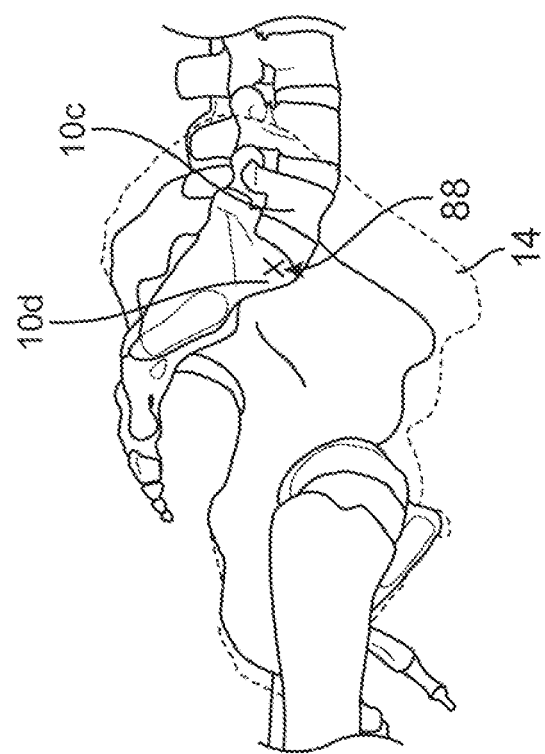
FIGS. 17a through 17g are an anterior-posterior view from the posterior, a lateral view, an isometric view, an anterior-posterior view from the anterior, an inlet view, a close-up inlet view, and an outlet view, respectively, of a variation of a method for placing an anchor wire at a target site.
Figure 17A:
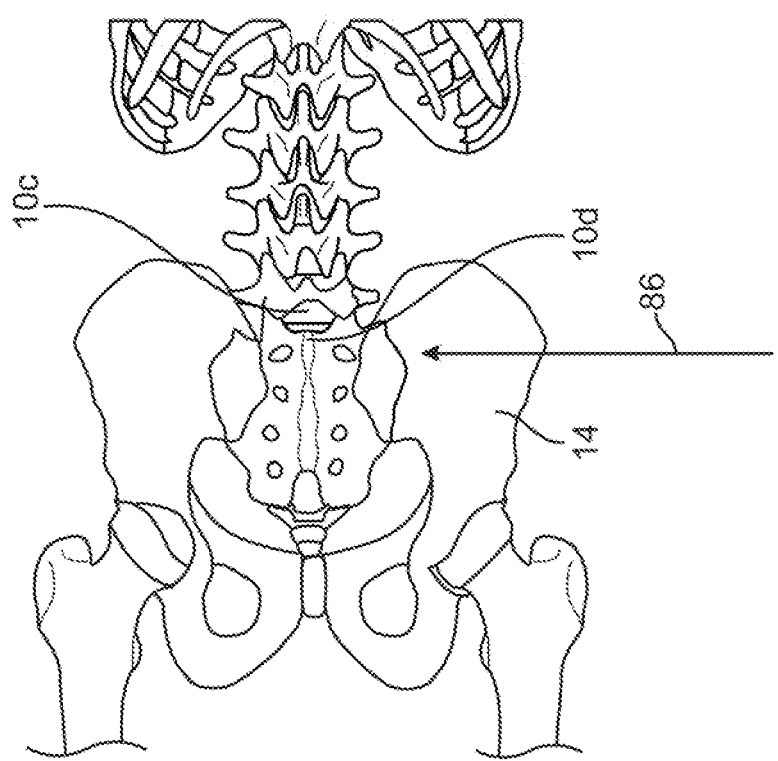
Figure 17C:
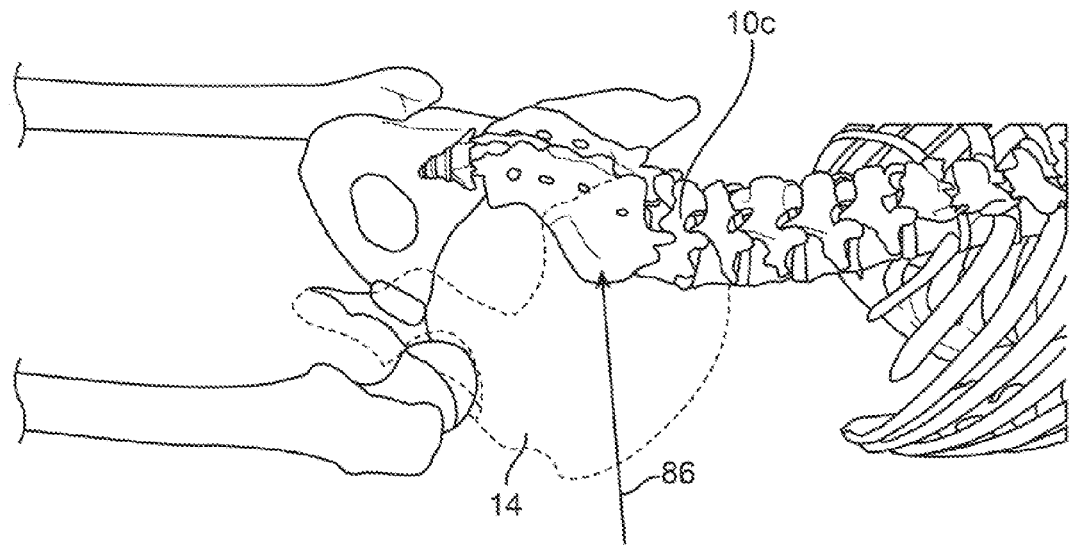
Figure 17D:
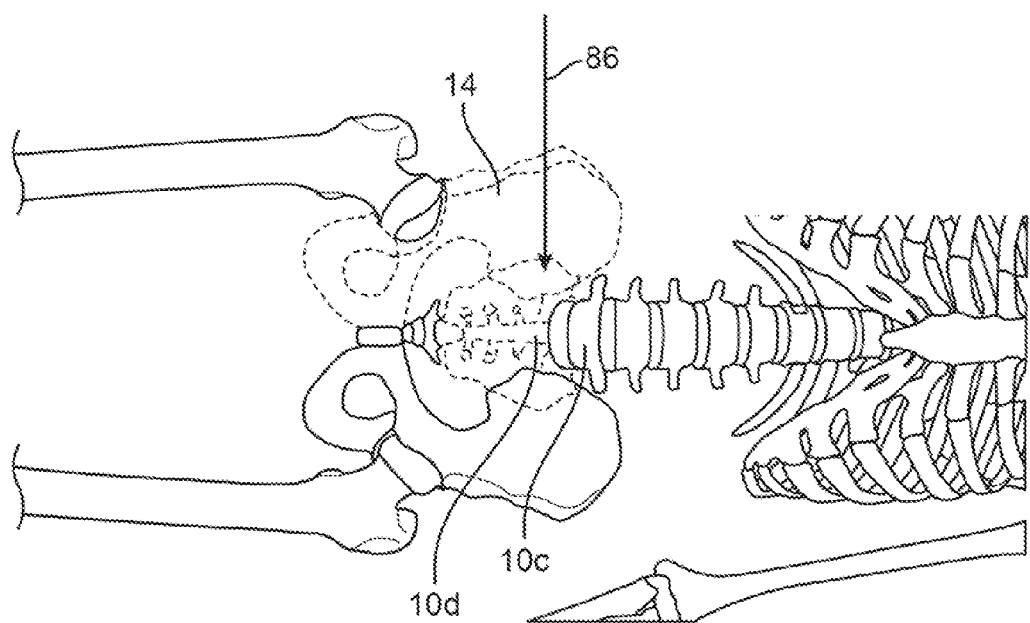
Figure 17F:
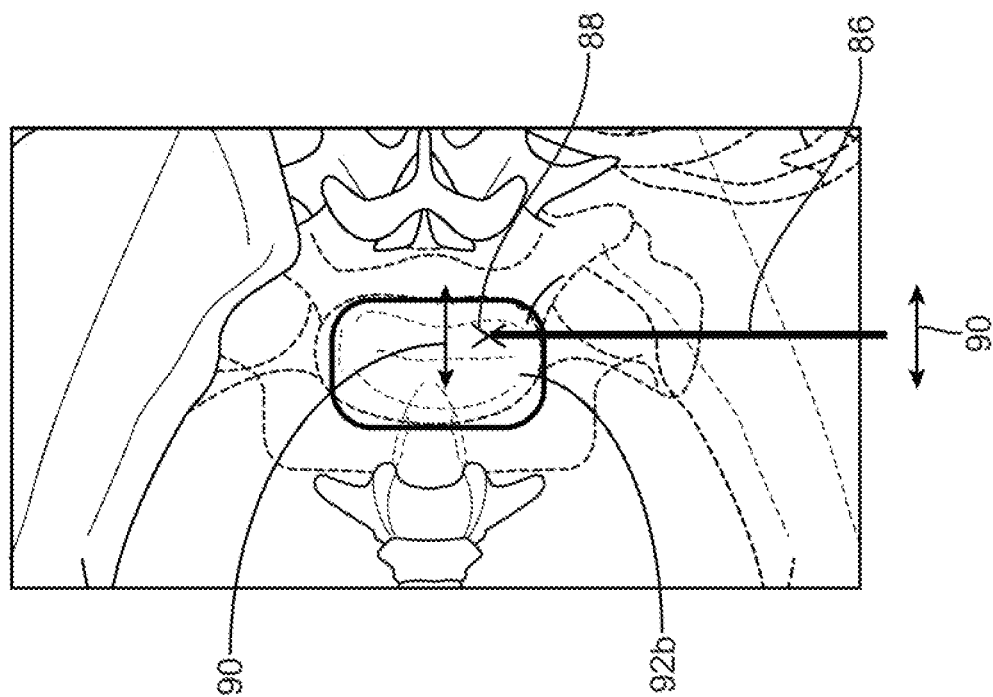
Figure 17E:
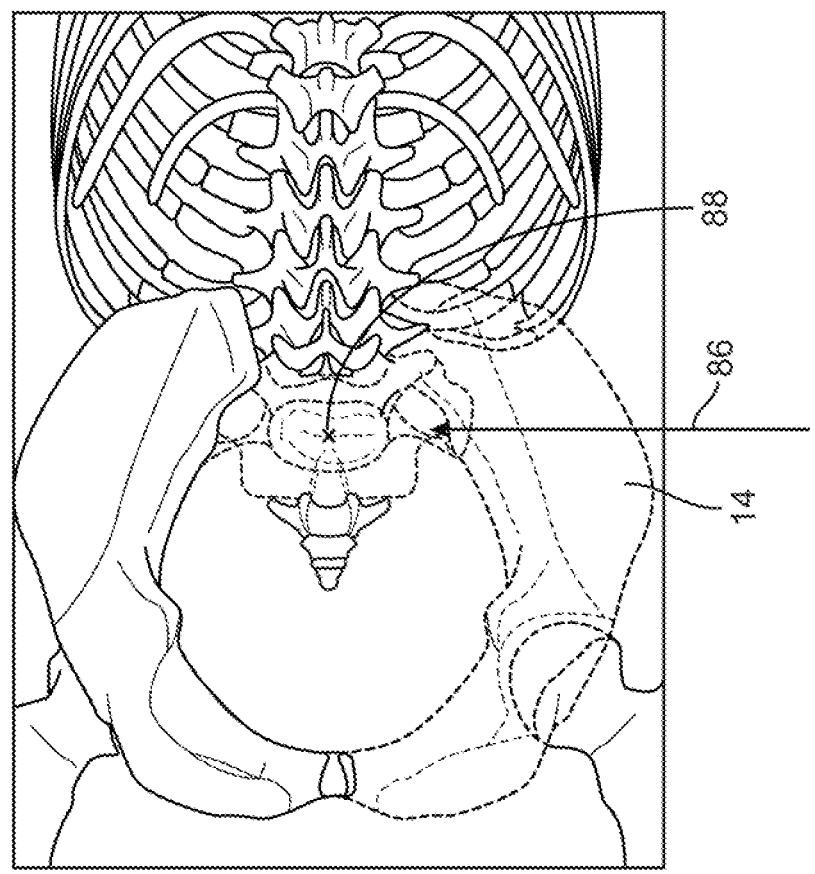
Figure 17G:
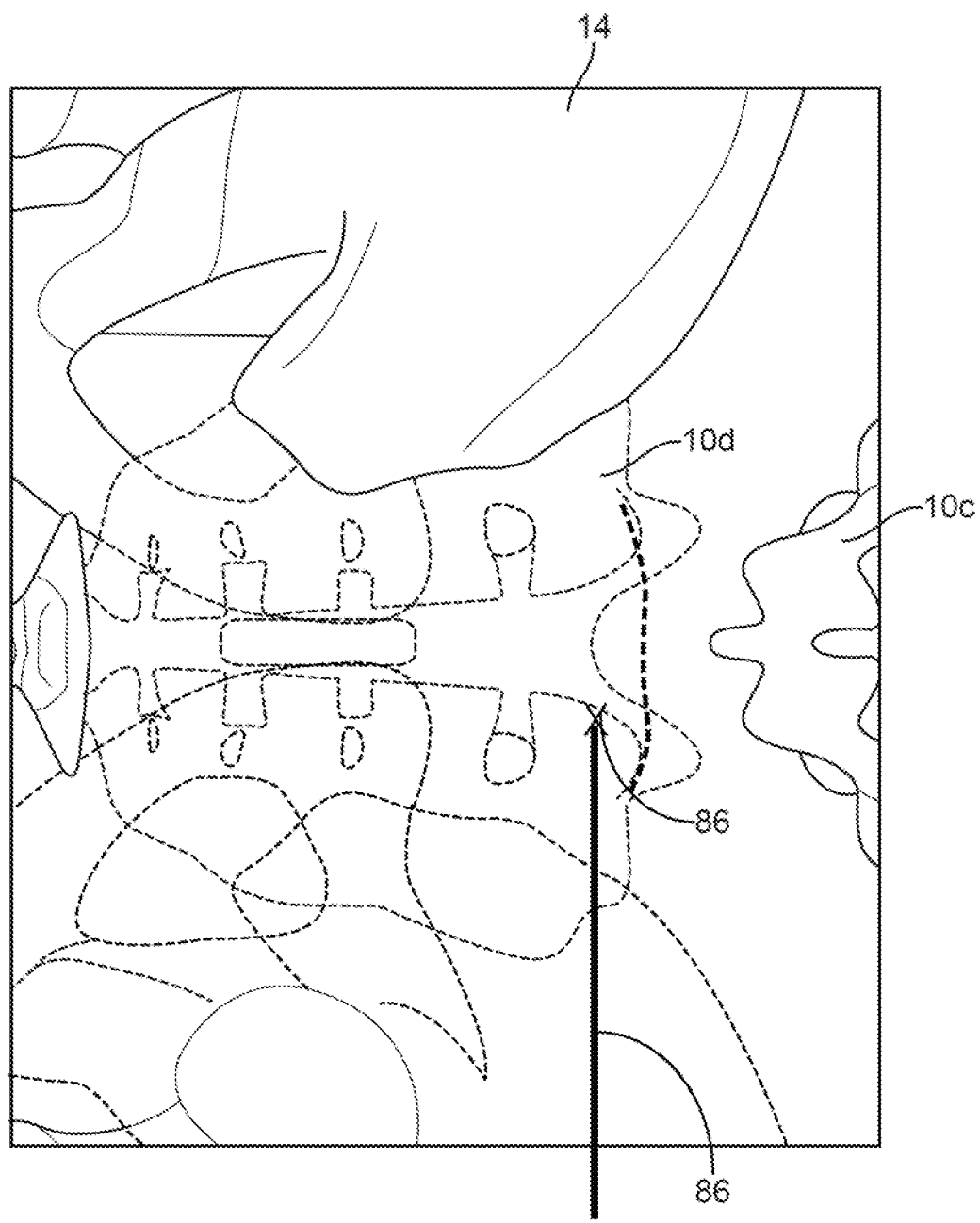

FIG. 17f illustrates an exemplary anterior to posterior target range, as shown by arrows 90, of a targeted placement of the anchor wire tip 74 in the S1 vertebra. For example, the resulting exit point of the access hole into the S1 endplate 92b can correlate to the desired position of the medial bone channel port. FIG. 17g illustrates an exemplary depth range, as shown by arrows, of a targeted placement of the anchor wire tip in the S1 vertebra.

The anchor wire can be delivered through the Ilium and/or ala.

Figure 18A:
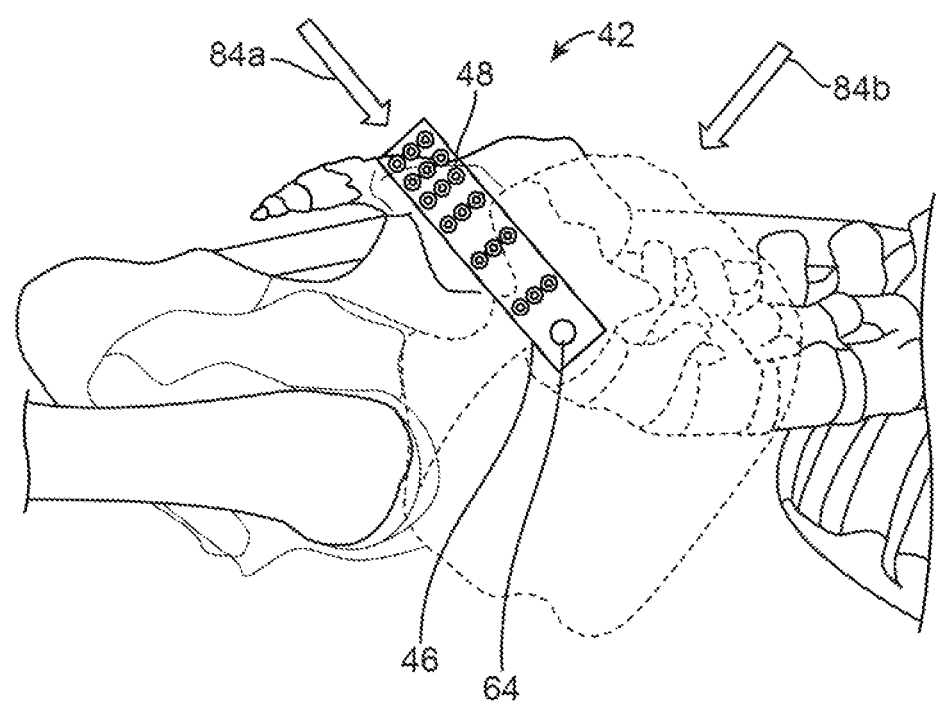
FIG. 18a is a lateral view of a variation of a method of placement of the wire guide, the anchor wire and the reamer wire, and an additional side perspective view of the guide tool for illustrative purposes.

FIG. 18a illustrates that after the anchor wire 64 is inserted into the target site, for example with the anchor wire tip 74 adjacent to the S1 vertebral body end plate 92b, the guide base 46 and the remainder of the guide tool 42 can be attached to the proximal end of the anchor wire 64 extending from the body. The anchor wire 64 can be fixed to the guide base 46 with the anchor lock 66. The guide tool is shown in partial see-through for illustrative purposes.

The reamer wire can then be inserted through a desired set of reamer wire holes. The approach angle of the reamer wire can be controlled by the selected reamer wire hole position. A position closer to the terminal end of the wire holder fixture can deliver the reamer wire at a higher angle relative to the anchor wire. The reamer wire can be inserted through the Ilium and ala, for example by pushing, turning or hammering, to position the reamer wire tip adjacent to or in contact with the anchor wire tip.

The reamer wire and/or the anchor wire can be delivered to the target site substantially entirely through bone after insertion into the Ilium (e.g., through superficial tissue and then into the Ilium and then through bone the entire length until the wire reaches the inside of the S1 vertebral body endplate).

The visualization guidance pin can be inserted into the visualization pin hole. The visualization guidance pin can extend parallel to the anchor wire on the outside of the patient. The visualization guidance pin can make no puncture or other wound in the patient during use.

Figure 18C:
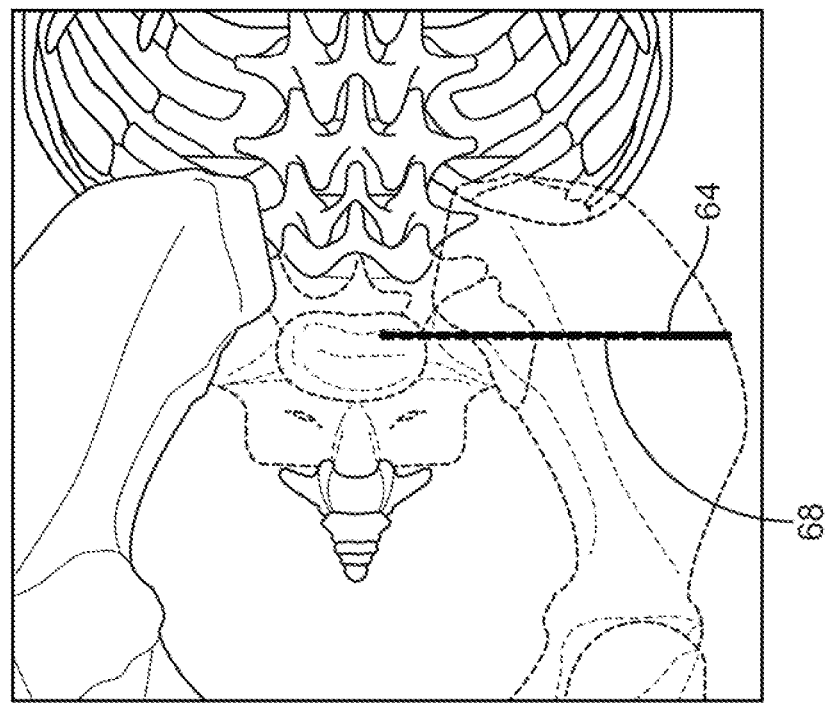
FIGS. 18b and 18c are outlet and inlet views, respectively, of a variation of the placement of the reamer wire.
Figure 18B:
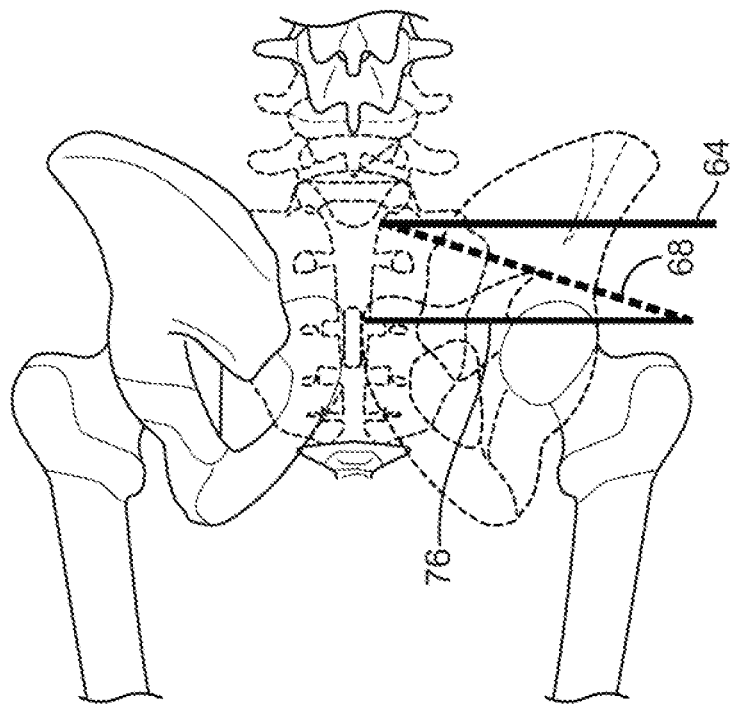

FIGS. 18b and 18c illustrate that the visualization guidance pin can form a plane with the reamer wire and the anchor wire in the inlet view to insure that the delivery of the reamer wire is in the desired orientation. The plane over the sacrum ala can be indicated, as shown in FIG. 18c, when the wires and pin align to form a single line in the inlet view. The guide tool can be rotated and/or the reamer pin can be inserted in a different reamer pin hole to correct for a misaligned reamer wire. (The reamer wire is shown as a dashed line in FIG. 18c for clarity.) The alignment indicated in FIGS. 18b and 18c can create the delivery path or check that the delivery path of the reamer wire passes directly through the ala when the reamer wire tip meets the anchor wire tip near the S1 end plate.

Figure 19:
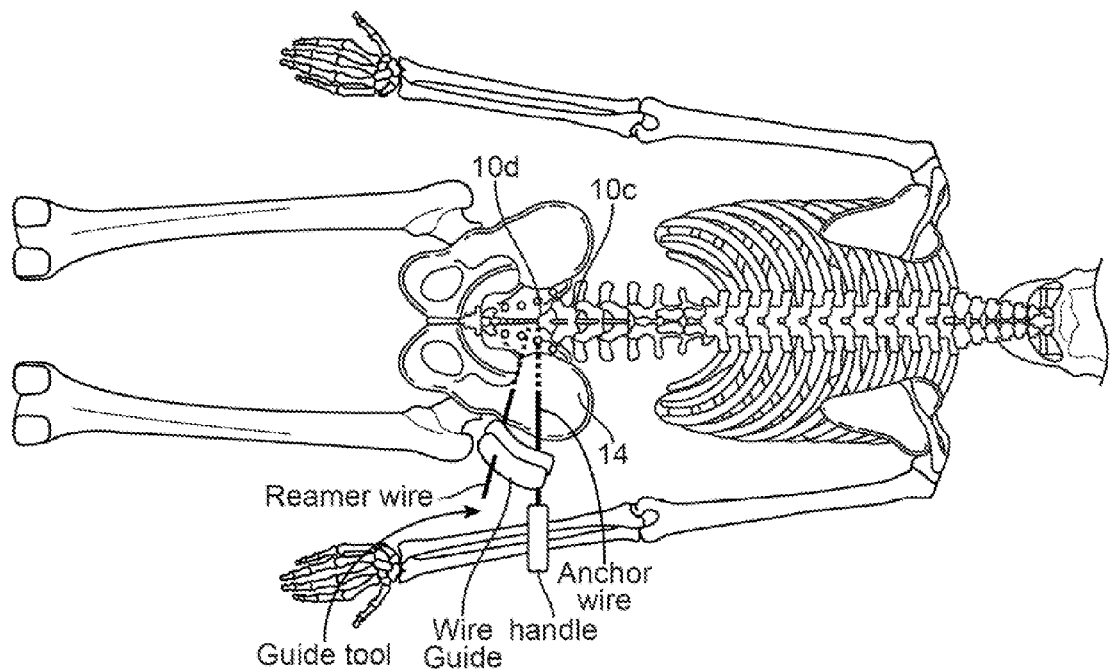
FIG. 19 is a posterior view of a variation of a method for placing the reamer wire with the anchor wire and wire guide tool.

FIG. 19 illustrates in an anterior-posterior view that the anchor wire and/pr reamer wire can pass through the Ilium, sacroiliac joint, ala, and sacrum. The wire holding fixture is labeled as "wire guide" in FIG. 19.

Figure 20:
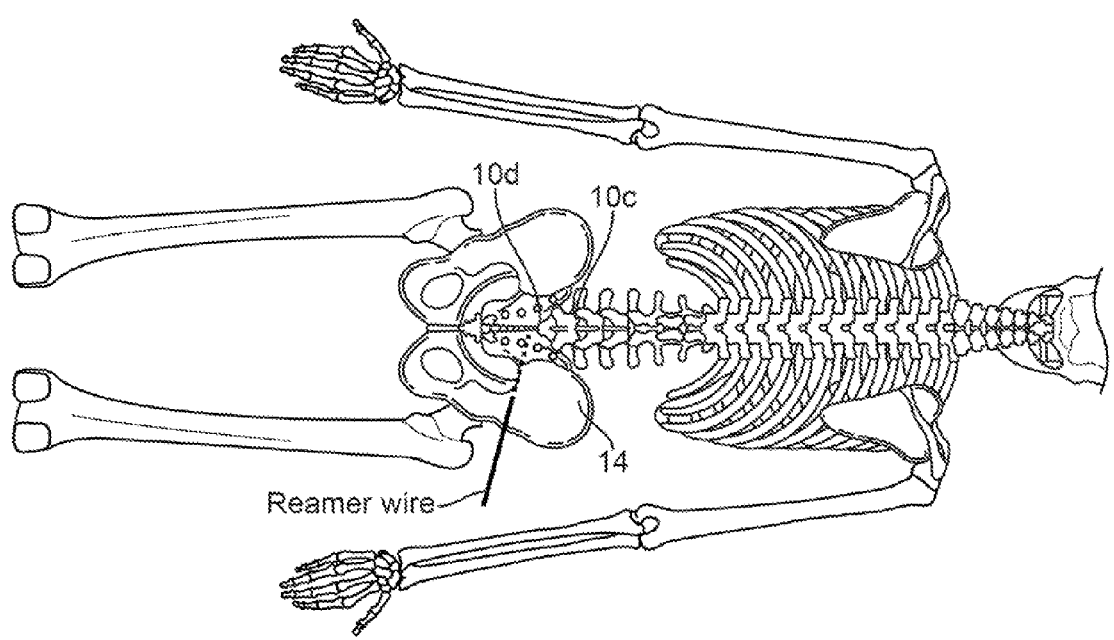
FIG. 20 is a posterior view of a skeleton with reamer wire in place and the wire guide and anchor wire removed from the target site.

FIG. 20 illustrates that the guide tool and anchor wire can be removed from the body. A cannulated reamer can then be inserted over the reamer wire, as described below.

Figure 21A:
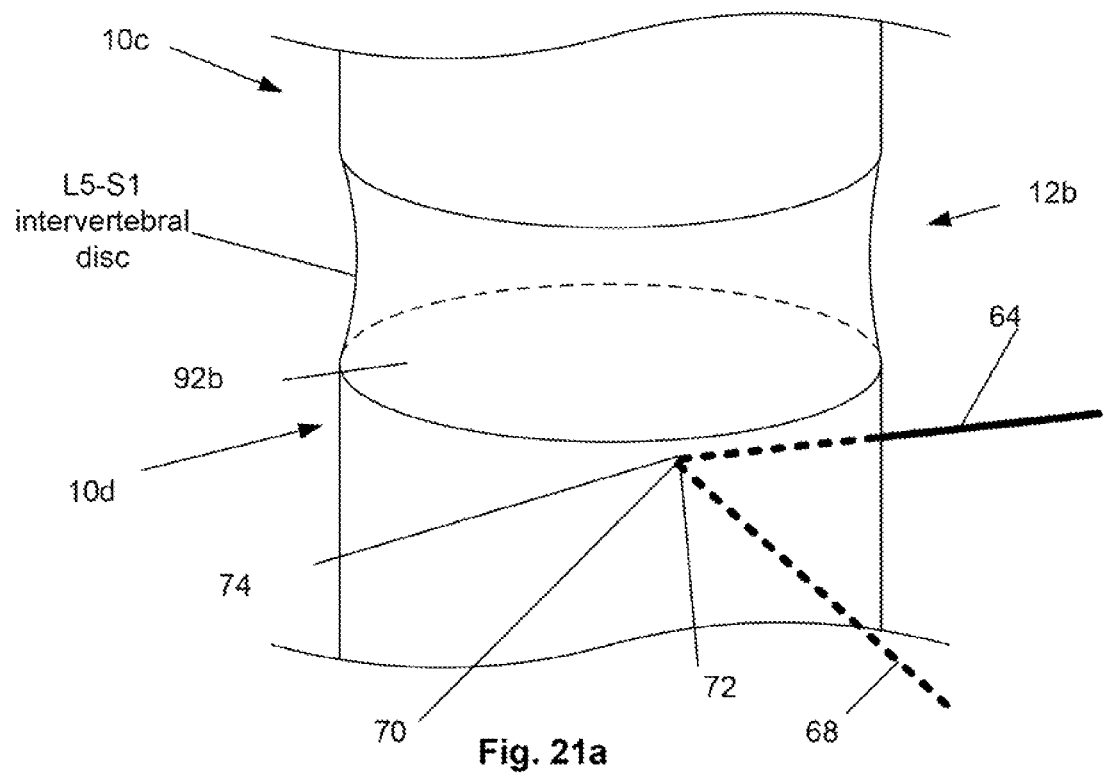
FIGS. 21a and 21b are perspective and sectional views of the target site during a variation of a method of placing the anchor wire and reamer wire in the spine.
Figure 21B:
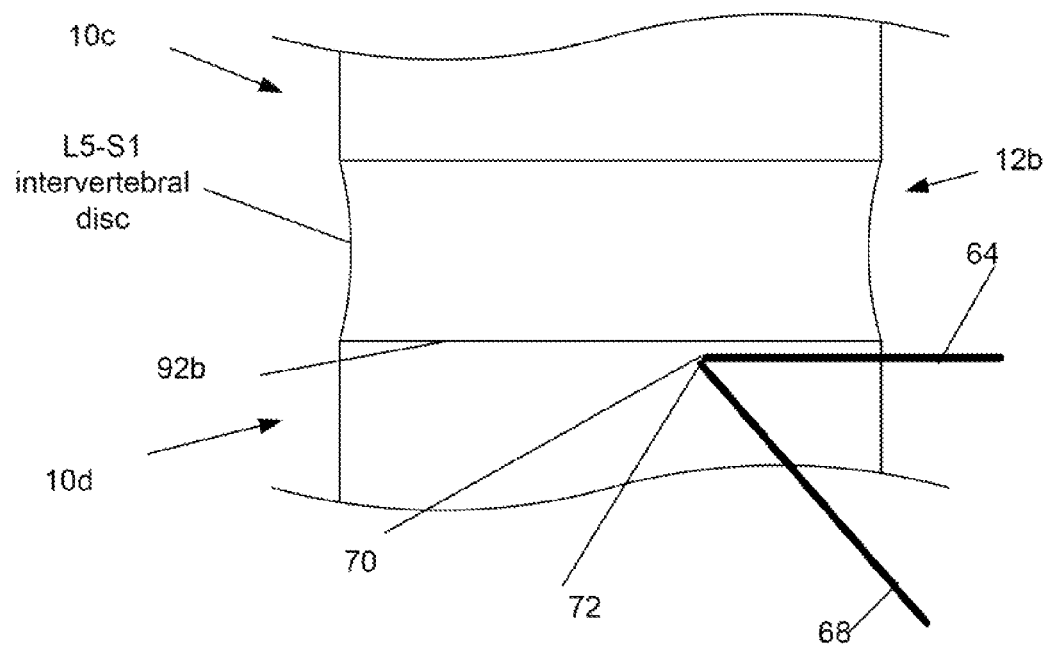

FIGS. 21a and 21b illustrate the reamer wire tip and anchor wire tip positioned at the guide target location. The guide target location, anchor wire tip, and reamer wire tip can be inside the sacrum bone adjacent to the endplate. The guide target location, anchor wire tip, and reamer wire tip can be (an exemplary distance) of about 5-10 mm under the endplate in the sacrum, for example in the cancellous bone of the sacrum.

Figure 22:
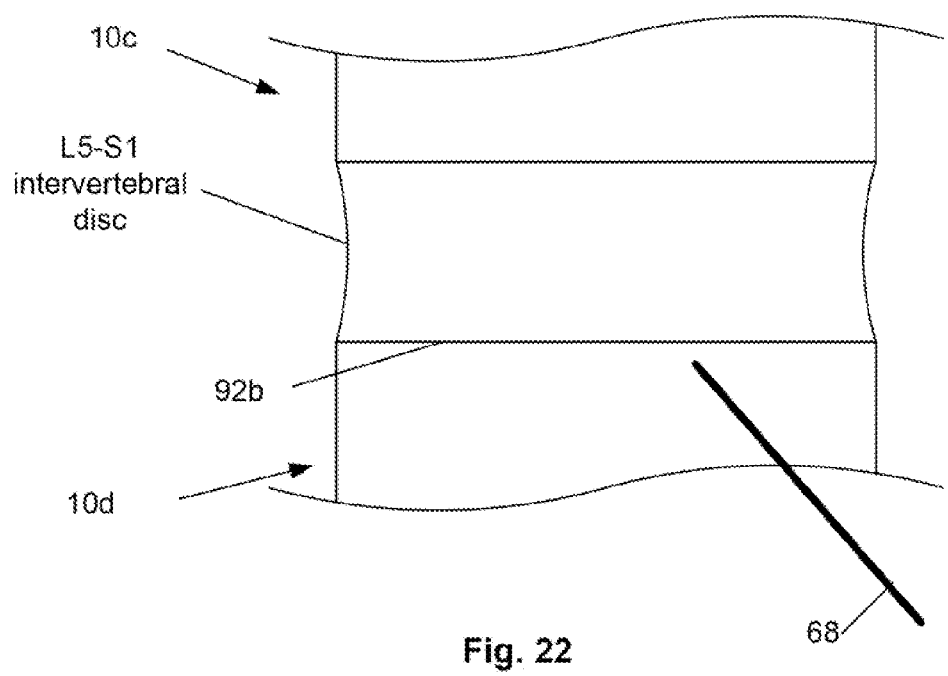
FIG. 22 illustrates a method of removing the anchor wire and leaving the reamer wire at the target site.

FIG. 22 illustrates that the anchor wire can be removed from the target site, leaving the reamer wire at the target site.

Figure 23A:
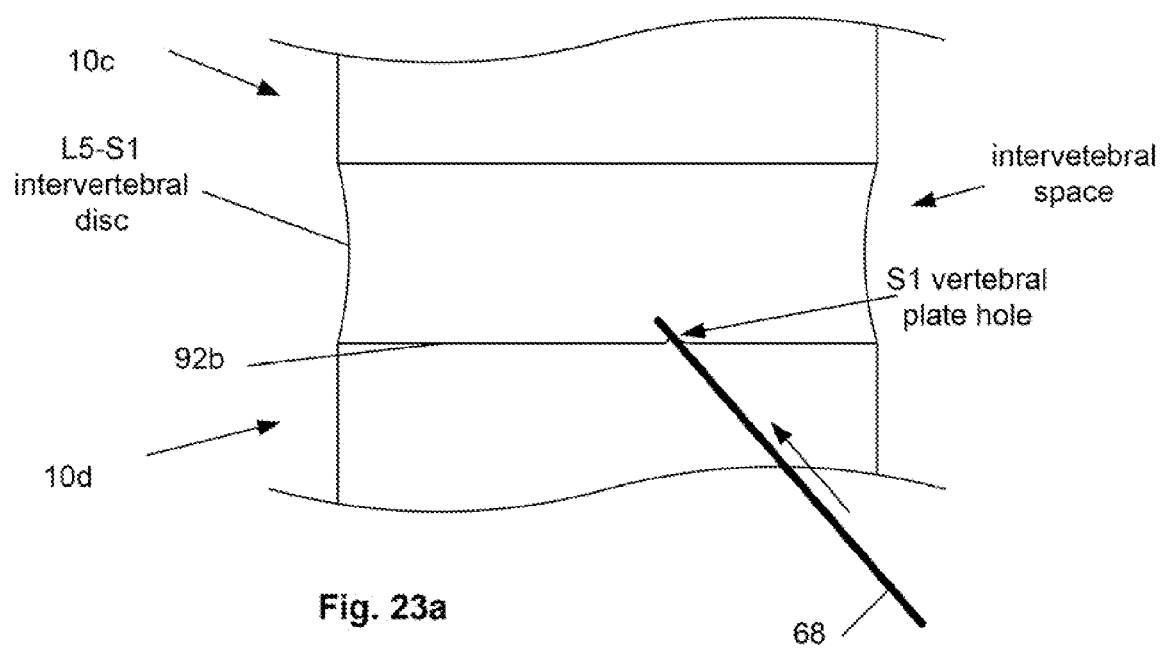
FIG. 23a illustrates a method for inserting the reamer wire into the intervertebral space.

FIG. 23a illustrates that the reamer wire can be forced, as shown by arrow, through the S1 vertebral end plate and into the intervertebral disc.

Figure 23B:
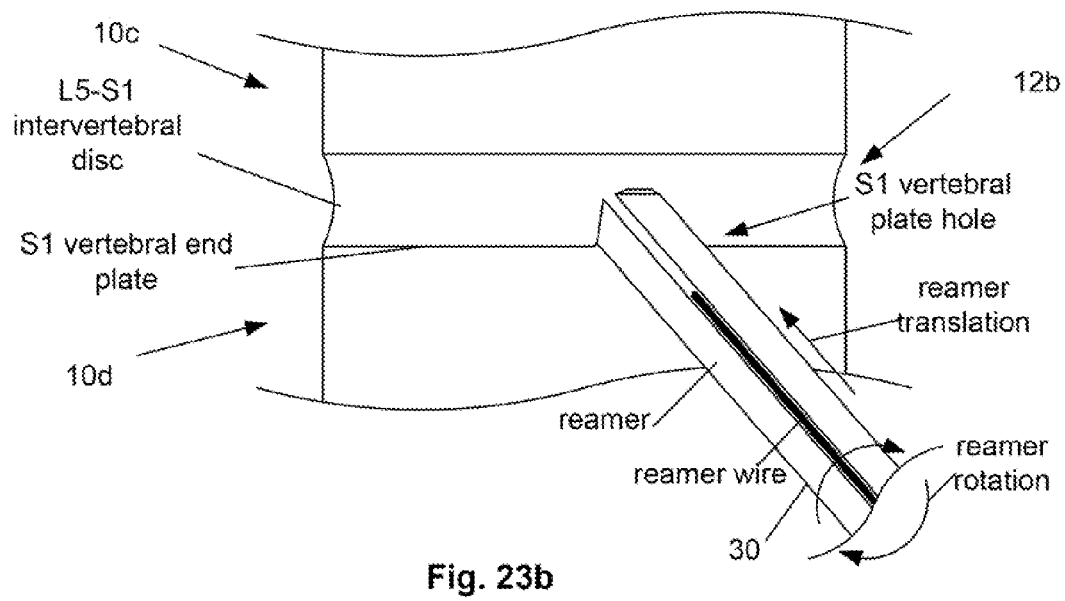
FIG. 23b illustrates a method for creating a bone channel and inserting a reamer into the intervertebral space.

FIG. 23b illustrates that a cannulated reamer can be translated, as shown by arrow, over the reamer wire. The reamer can enter the intervertebral space. The reamer can open a hole in the S1 vertebral plate, or the S1 vertebral plate hole can be opened first by the reamer wire, as shown in FIG. 23a.

The reamer can rotate, as shown by arrows, reaming a bone channel through the pathway defined by the reamer wire. The bone channel can extend from the Ilium to the S1 vertebral end plate. The reamer can have a reamer diameter from about 10 mm to about 23 mm, for example about 15.5 mm. The bone channel can have a bone channel diameter approximately equal to the reamer diameter.

During reaming, the reamer can experience more resistance from the cortical S1 vertebral end plate, indicating to the user that the reamer is approaching the intervertebral space (due to the change in bone density). The reaming can be performed with a visualization technique (e.g., fluoroscopy) to indicate the position of the reamer with respect to the surrounding anatomy. The reamer can ream the bone channel into the L5 vertebra or stop short of reaming the L5 vertebra (as shown). The bone reamed during the reaming process can be preserved for use later as a filler. The reamer can be threaded and/or have one or more cutting blades extending radially outward. Irrigation (e.g., or saline solution, anesthetic, antibiotics, or combinations thereof) and suction can be delivered to the treatment site before, during and/or after reaming, wire insertion, support device insertion, bone filler delivery, or combinations thereof.

Figure 24:
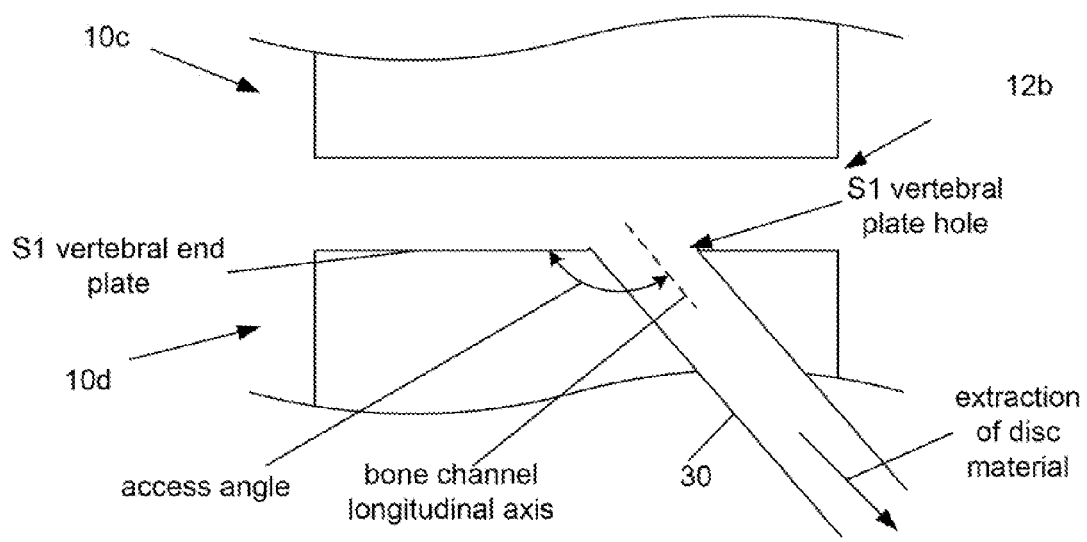
FIG. 24 illustrates a variation of the results from a discectomy performed on the target intervertebral space.

FIG. 24 illustrates that a discectomy can be performed through the bone channel. The L5-S1 intervertebral disc can be morselized and removed by suction through the bone channel.

The bone channel can have a bone channel longitudinal axis. The bone channel longitudinal axis can form an access angle with respect to the plane defined by the S1 vertebral end plate. The access angle can be from about 1° to about 90°, more narrowly from about 3° to about 40°, yet more narrowly from about 5° to about 30°, yet more narrowly from about 10° to about 25°, for example about 15°, about 20°, or about 25°.

Figures 25A, 25B, 25C, 25D:
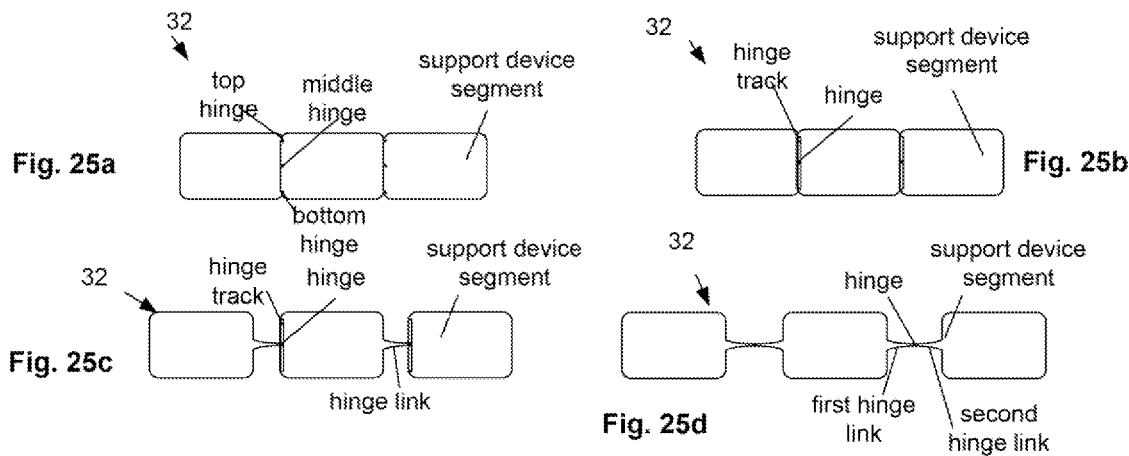
FIGS. 25a through 25d illustrate variations of the support device.

FIG. 25a illustrates that the support device can have one, two, three or more support device segments in a linear arrangement rotatably attached to each other. The support device segments can have rectangular configurations. The support device segments can be rigid and/or flexible. For example, the support device segments can be configured to expand in height when compressed in length. After insertion into an intervertebral space, the support device segments can be longitudinally compressed and expand in height to fill the intervertebral space.

The support device segments can be attached to adjacent support device segments with one, two or three hinges, such as top hinges, middle hinges, bottom hinges, or a combination thereof. Although single hinge attachments between segments can be used, a multiple hinge attachment can be used when the hinges away from the rotation can detach, such as pop-fit hinges.

FIG. 25b illustrates that the adjacent segments can be rotatably attached by a single hinge. The hinge can be in a hinge track that can allow the hinge to translate vertically (as shown) or longitudinally with respect to the support device segment.

FIG. 25c illustrates that that support device segments can have a hinge link extending from a single end of the segment. The hinge link can have the hinge at the terminal end of the hinge link. The hinge link can have a smaller height than the remainder of the support device, for example allowing adjacent support device segments greater range of rotational motion with respect to the adjacent support device segment. For example, the support device segments can rotate up to about 300°, more narrowly up to about 270°, yet more narrowly up to about 240°, before interference fitting against the adjacent segment.

FIG. 25d illustrates that the support device segments can have a first hinge link extending from one end of the segment and a second hinge link extending from a second end of the segment. The hinge links from adjacent segments can attach to each other at a hinge. The support device segments can rotate up to about 330°, more narrowly up to about 270°, before interference fitting against the adjacent segment.

Figure 26A:
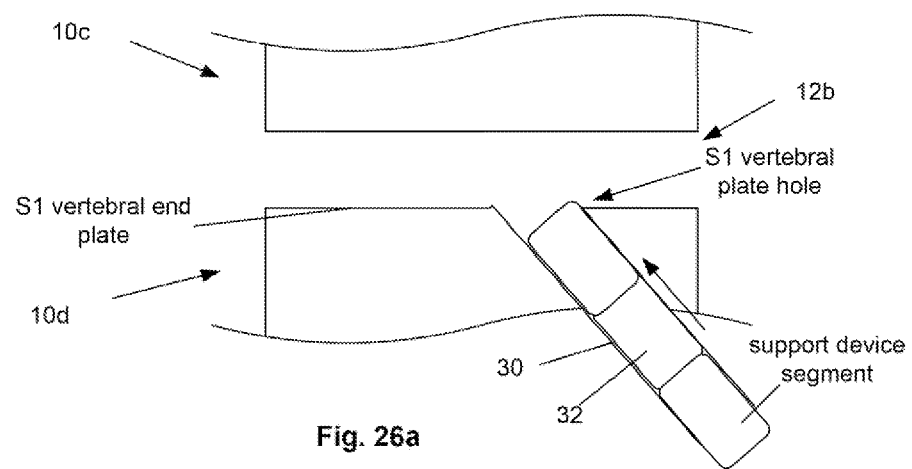
FIGS. 26a through 26d illustrate a variation of a method for delivering a variation of the support device through the bone channel, into the intervertebral space, and filling the bone channel.
Figure 26B:
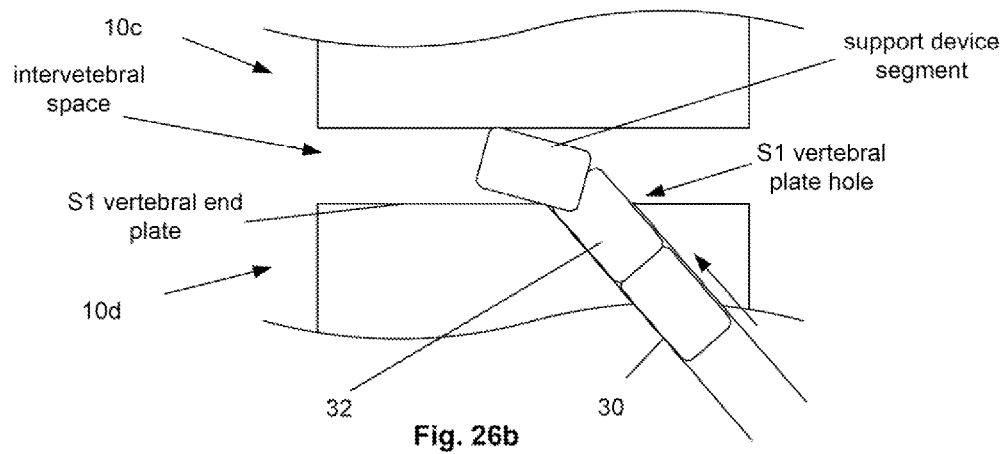

FIG. 26a illustrates that the support device can be inserted, as shown in translation by the arrow, through the bone channel. FIG. 26b illustrates that the support device can articulate as the support device enters the intervertebral space from the bone channel. The spine can be placed in tension and/or the L5 vertebra can be distended from the S1 vertebra, for example to hold or increase the height of the L5-S1 intervertebral space before the support device is inserted into the intervertebral space. For example, the patient's shoulders and legs or hip can be pulled apart, remote mechanical retractors (e.g., a scissors jack) can be inserted through the bone channel and deployed in the intervertebral space, a high-strength balloon can be inserted through the bone channel into the intervertebral space and be inflated, or a combination thereof to move the L5 end plate away from the S1 end plate.

The support device can enter the intervertebral space free of obstruction or can interference fit against (i.e., bump into) the L5 vertebral end plate, further passively articulating the support device segments and redirecting the support device further into the intervertebral bone space. The support device segments can be actively articulatable with respect to each other, for example by control through releasable cables or wires extending through a hollow channel in the support device and connected to the individual support device segments.

Figure 26C:
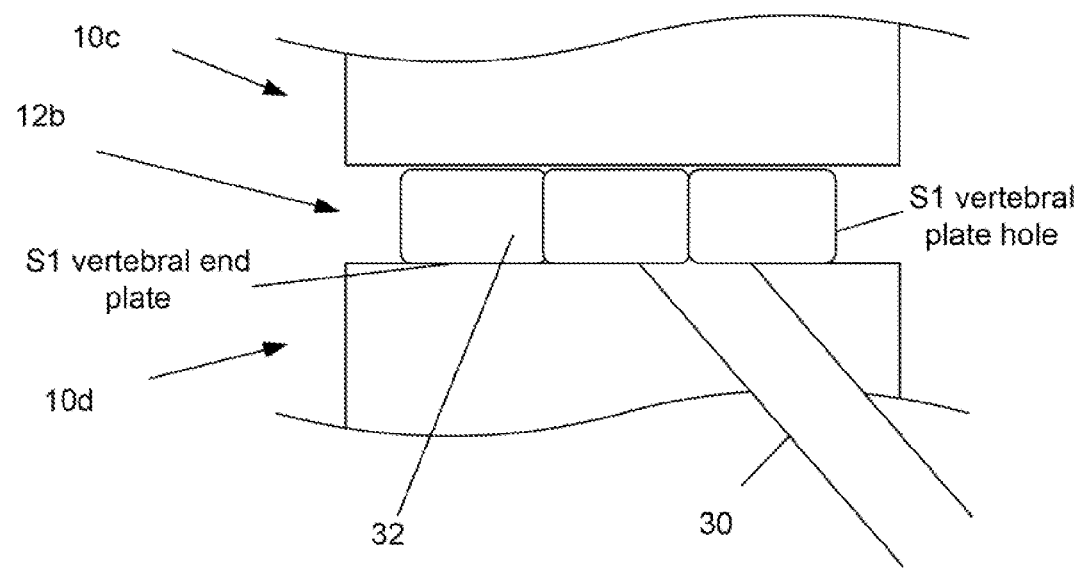

FIG. 26c illustrates that the support device can be completely positioned within the intervertebral space. The support device can be the entire width of the intervertebral space or less than the entire width of the intervertebral space (as shown). The support device can be longitudinally compressed, which for example can result in height expansion of the support device (such as for support devices with a structure having expandable struts or compressible expansion ramps between support device end plates).

A hollow channel or cavity in the support device and/or the intervertebral space outside of the support device can be filled with a filler, such as morselized bone (including autograft of the bone removed to create the hone channel), BMP, any material listed herein, or combinations thereof.

The support device can be fixed to the end plates with screws, staples, anchors, brads, hooks, epoxy or combinations thereof. For example, anchoring screws can be delivered through the bone channel.

Figure 26D:
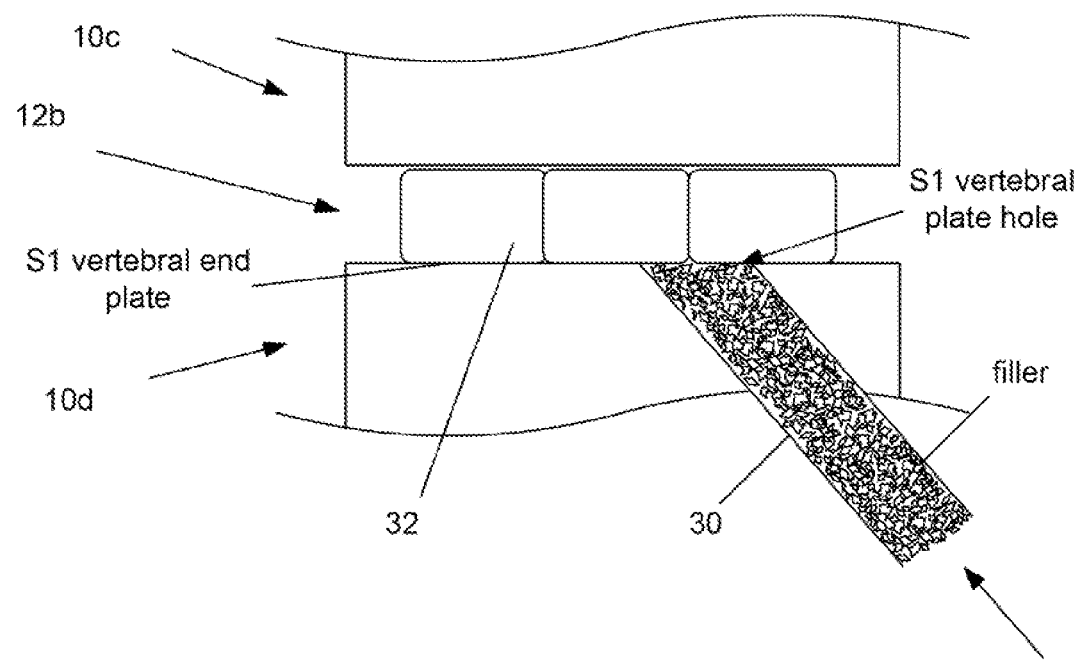

FIG. 26d illustrates that the bone channel can be filled with a bone channel filler, such as morselized bone (including autograft of the bone removed to create the bone channel), BMP, any material listed herein, or combinations thereof.

FIG. 27a illustrates that the support device segments can each have proximal and distal chamfers, bevels, notches. The proximal and distal chamfers can be on the top side of the support device segments.

FIG. 27b illustrates that the top of the distal-most support device segment of the support device can have a distal chamfer. The top of the proximal-most support device segment of the support device can have a proximal chamfer. The remainder of the support device segments can have no significant chamfers.

FIG. 27c illustrates that the tops of the distal-most and proximal-most support device segments of the support device can have distal chamfers and proximal chamfers. The remainder of the support device segments can have no significant chamfers.

FIG. 28a illustrates that the support device can be inserted, as shown in translation by the arrow, through the bone channel. FIG. 28b illustrates that the support device can articulate as the support device enters the intervertebral space from the bone channel. The support device can move clear of the L5 vertebral end plate during the initial insertion, for example the anterior chamfer of the anterior support device segment can allow the support device segments to initial move into the intervertebral space without pressing against the L5 end plate. During continue insertion of the support device, the support device segments can press against the L5 intervertebral end plate.

Figure 28C:
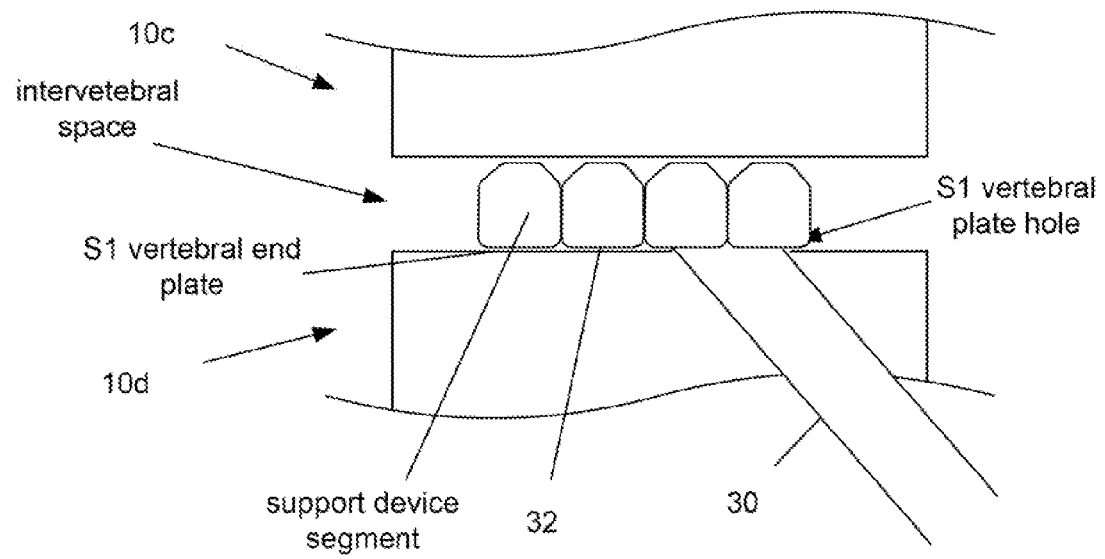

FIG. 28c illustrates that similar to the support device shown and described in FIG. 26c, the support device can be positioned in the intervertebral space. The support device can be fixed to the surrounding tissue. The support device and/or the intervertebral space can be filled with filler.

Figure 28D:
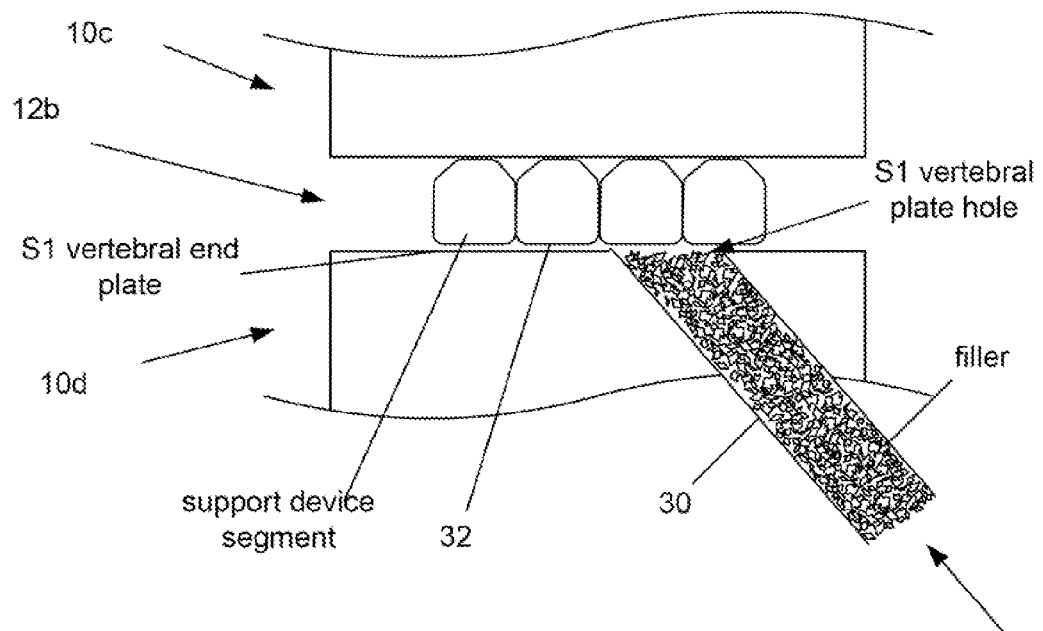

FIG. 28d illustrates that similar to the support device shown and described in FIG. 26d, the bone channel can be filled with filler.

Figure 29A:
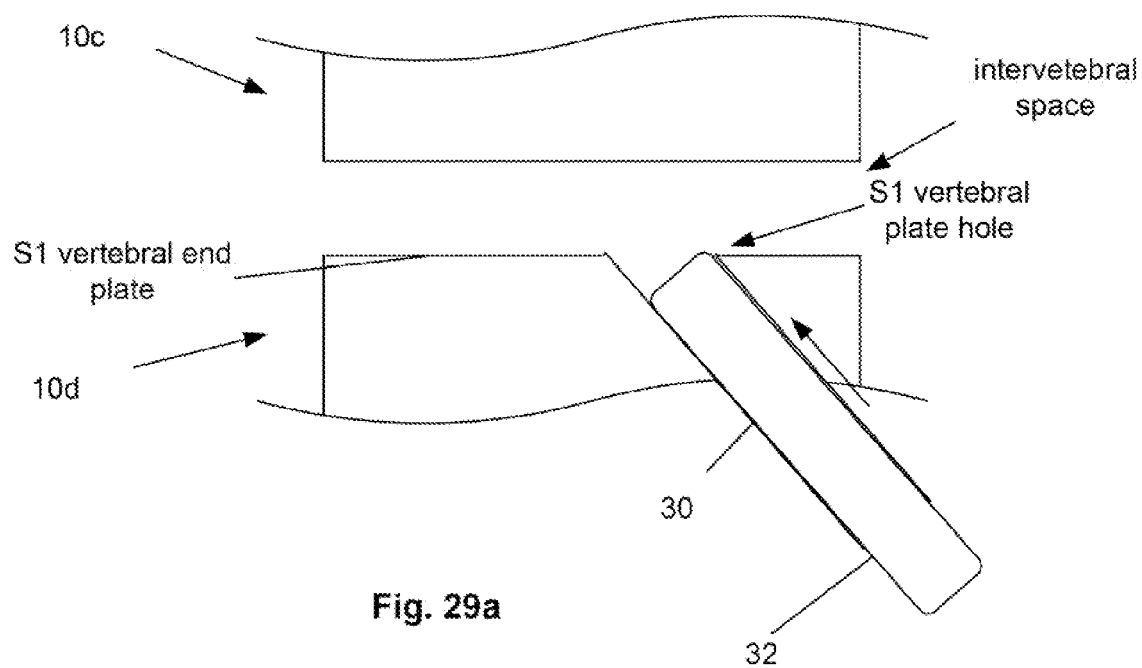
FIGS. 29a through 29d illustrate a variation of a method for delivering a variation of the support device through the bone channel, into the intervertebral space, and filling the bone channel.
Figure 29B:
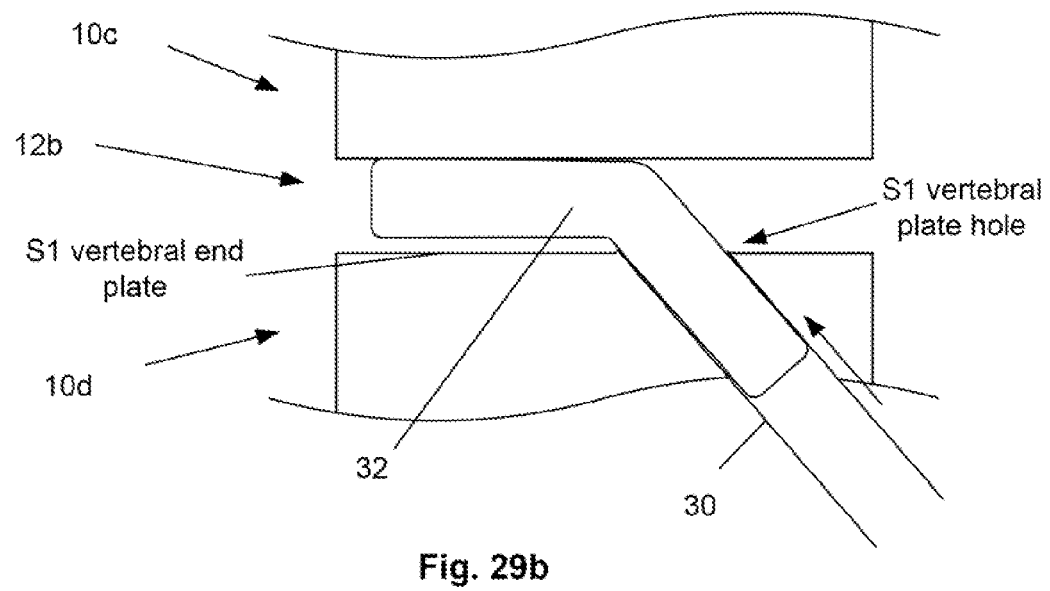

FIGS. 29a through 29d illustrate that the support device can be flexible. The support device can have one or more support device segments (shown as a single segment for illustrative purposes). The support device can be elastically or plastically deformable during insertion from the bone channel intro the intervertebral space. As shown in FIG. 29b, the support device can flexible, and elastically (i.e., resiliently) or plastically bend around the turn from the bone channel into the intervertebral space.

Figure 29C:
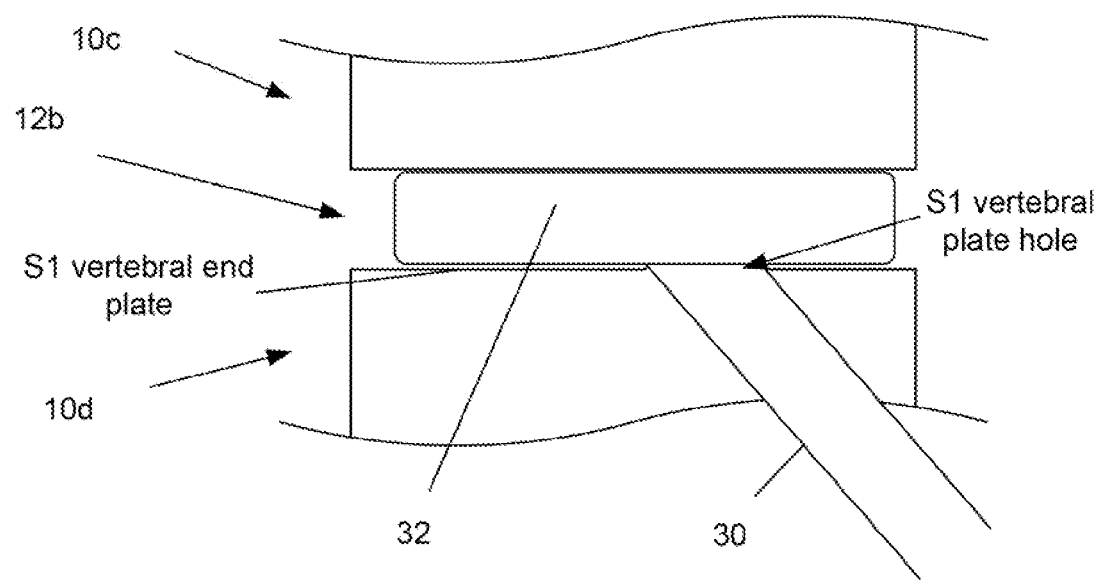

FIG. 29c illustrates that similar to the support device shown and described in FIG. 26c, the support device can be positioned in the intervertebral space. The support device can be fixed to the surrounding tissue. The support device and/or the intervertebral space can be filled with filler.

Figure 29D:
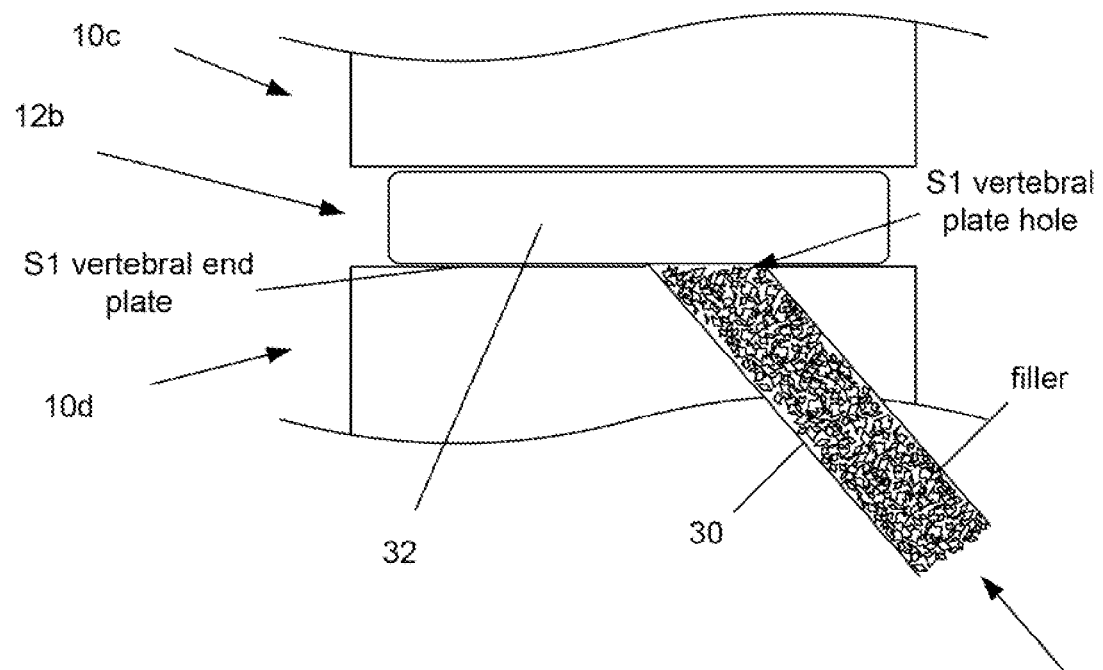

FIG. 29d illustrates that similar to the support device shown and described in FIG. 26d, the bone channel can be filled with filler.

Any or all elements of the device and/or other devices or apparatuses described herein can be made from, for example, a single or multiple stainless steel alloys, nickel titanium alloys (e.g., Nitinol), cobalt-chrome alloys (e.g., ELGILOY® from Elgin Specialty Metals, Elgin, Ill.; CONICHROME® from Carpenter Metals Corp., Wyomissing, Pa.), nickel-cobalt alloys (e.g., MP35N® from Magellan Industrial Trading Company, Inc., Westport, Conn.), molybdenum alloys (e.g., molybdenum TZM alloy, for example as disclosed in International Pub. No. WO 03/082363 A2, published 9 Oct. 2003, which is herein incorporated by reference in its entirety), tungsten-rhenium alloys, for example, as disclosed in International Pub. No. WO 03/082363, polymers such as polyethylene teraphathalate (PET)/polyester (e.g., DACRON® from E. I. Du Pont de Nemours and Company, Wilmington, Del.), polypropylene, (PET), polytetrafluoroethylene (PTFE), expanded PTFE (ePTFE), polyether ketone (PEK), polyether ether ketone (PEEK), poly ether ether ketone ketone (PEKK) (also poly aryl ether ketone ketone), nylon, polyether-block co-polyamide polymers (e.g., PEBAX® from ATOFINA, Paris, France), aliphatic polyether polyurethanes (e.g., TECOFLEX® from Thermedics Polymer Products, Wilmington, Mass.), polyvinyl chloride (PVC), polyurethane, thermoplastic, fluorinated ethylene propylene (FEP), absorbable or resorbable polymers such as polyglycolic acid (PGA), polylactic acid (PLA), polycaprolactone (PCL), polyethyl acrylate (PEA), polydioxanone (PDS), and pseudo-polyamino tyrosine-based acids, extruded collagen, silicone, zinc, echogenic, radioactive, radiopaque materials, a biomaterial (e.g., cadaver tissue, collagen, allograft, autograft, xenograft, bone cement, morselized bone, osteogenic powder, beads of bone) any of the other materials listed herein or combinations thereof. Examples of radiopaque materials are barium sulfate, zinc oxide, titanium, stainless steel, nickel-titanium alloys, tantalum and gold.

Any or all elements of the device and/or other devices or apparatuses described herein, can be, have, and/or be completely or partially coated with agents and/or a matrix a matrix for cell ingrowth or used with a fabric, for example a covering (not shown) that acts as a matrix for cell ingrowth. The matrix and/or fabric can be, for example, polyester (e.g., DACRON® from E. I. Du Pont de Nemours and Company, Wilmington, Del.), polypropylene, PTFE, ePTFE, nylon, extruded collagen, silicone or combinations thereof.

The device and/or elements of the device and/or other devices or apparatuses described herein and/or the fabric can be filled, coated, layered and/or otherwise made with and/or from cements, fillers, glues, and/or an agent delivery matrix known to one having ordinary skill in the art and/or a therapeutic and/or diagnostic agent. Any of these cements and/or fillers and/or glues can be osteogenic and osteoinductive growth factors.

Examples of such cements and/or fillers includes bone chips, demineralized bone matrix (DBM), calcium sulfate, coralline hydroxyapatite, biocoral, tricalcium phosphate, calcium phosphate, polymethyl methacrylate (PMMA), biodegradable ceramics, bioactive glasses, hyaluronic acid, lactoferrin, bone morphogenic proteins (BMPs) such as recombinant human bone morphogenetic proteins (rhBMPs), other materials described herein, or combinations thereof.

The agents within these matrices can include any agent disclosed herein or combinations thereof, including radioactive materials; radiopaque materials; cytogenic agents; cytotoxic agents; cytostatic agents; thrombogenic agents, for example polyurethane, cellulose acetate polymer mixed with bismuth trioxide, and ethylene vinyl alcohol; lubricious, hydrophilic materials; phosphor cholene; anti-inflammatory agents, for example non-steroidal anti-inflammatories (NSAIDs) such as cyclooxygenase-1 (COX-1) inhibitors (e.g., acetylsalicylic acid, for example ASPIRIN® from Bayer AG, Leverkusen, Germany; ibuprofen, for example ADVIL® from Wyeth, Collegeville, Pa.; indomethacin; mefenamic acid), COX-2 inhibitors (e.g., VIOXX® from Merck & Co., Inc., Whitehouse Station, N.J.; CELEBREX® from Pharmacia Corp., Peapack, N.J.; COX-1 inhibitors); immunosuppressive agents, for example Sirolimus (RAPAMUNE®, from Wyeth, Collegeville, Pa.), or matrix metalloproteinase (MMP) inhibitors (e.g., tetracycline and tetracycline derivatives) that act early within the pathways of an inflammatory response. Examples of other agents are provided in Walton et al, Inhibition of Prostoglandin $E_2$ Synthesis in Abdominal Aortic Aneurysms, Circulation, Jul. 6, 1999, 48-54; Tambiah et al, Provocation of Experimental Aortic Inflammation Mediators and *Chlamydia Pneumoniae*, Brit. J. Surgery 88 (7), 935-940; Franklin et al, Uptake of Tetracycline by Aortic Aneurysm Wall and Its Effect on Inflammation and Proteolysis, *Brit. J. Surgery* 86 (6), 771-775; Xu et al, Spl Increases Expression of Cyclooxygenase-2 in Hypoxic Vascular Endothelium, *J. Biological Chemistry* 275 (32) 24583-24589; and Pyo et al, Targeted Gene Disruption of Matrix Metalloproteinase-9 (Gelatinase B) Suppresses Development of Experimental Abdominal Aortic Aneurysms, *J. Clinical Investigation* 105 (11), 1641-1649 which are all incorporated by reference in their entireties.

PCT Application Nos. PCT/US2011/000974, filed 27 May 2011; and PCT/US2011/048992, filed 24 Aug. 2011; and U.S. Provisional Application Nos. 61/349,151, filed 27 May 2010; 61/376,626, filed 24 Aug. 2010, are all incorporated by reference herein in their entireties.

Any elements described herein as singular can be pluralized (i.e., anything described as "one" can be more than one). Any species element of a genus element can have the characteristics or elements of any other species element of that genus. The above-described configurations, elements or complete assemblies and methods and their elements for carrying out the invention, and variations of aspects of the invention can be combined and modified with each other in any combination.

We claim:

1. A method for guided deployment of a biological implant support device comprising:

locating a spinal location within a vertebral bone with a first wire tip of a first wire, wherein the locating comprises positioning the first wire tip at the spinal location;

positioning a frame on the first wire;

inserting a second wire having a second wire tip through the frame;

visualizing the first wire and the second wire, wherein the visualizing comprises visualizing with an imaging system;

rotating the frame around the first wire so the first wire and second wire form a single line when viewed by the imaging system;

further inserting the second wire through the frame to the spinal location;

reaming through bone along a path of the second wire, wherein reaming comprises creating a bone channel;

inserting a support device through the bone channel, wherein inserting comprises positioning the support device in an intervertebral location;

supporting with the support device a first vertebral end plate on a first side of the intervertebral location, and supporting with the support device a second vertebral end plate on a second side of the intervertebral location; and positioning a third wire parallel with the first wire, wherein the second wire is positioned between the first wire and the third wire.

2. The method of claim 1, wherein the bone channel accesses the intervertebral location, and wherein a longitudinal axis of the bone channel forms an access angle with respect to the first vertebral end plate, and wherein the access angle is less than 45°.

3. The method of claim 2, wherein the access angle is less than 30°.

4. The method of claim 2, wherein the access angle is less than 25°.

5. The method of claim 1, wherein the support device is positioned entirely within the intervertebral space.

6. The method of claim 1, wherein the support device is comprises a first segment and a second segment and wherein the first segment is rotatably attached to a second segment, wherein the inserting of the support device comprises rotating the first segment with respect to the second segment.

7. The method of claim 1, further comprising visualizing the third wire.

8. The method of claim 1, wherein the third wire is inserted through the frame.

9. The method of claim 8, wherein the first wire is inserted through the frame.

10. The method of claim 1, wherein the third wire does not enter a body of a patient upon which the support device is inserted.

11. The method of claim 1, wherein the first wire extends through a first port in a wire guide, and wherein the second wire extends through a second port in the wire guide, and wherein the wire guide has a third port configured to receive the second wire.

12. The method of claim 11, wherein the third wire extends through the wire guide.

13. The method of claim 11, wherein the third port is angularly offset on the wire guide from the second port.

14. The method of claim 11, wherein the third port is laterally adjacent on the wire guide to the second port.

15. The method of claim 1, wherein the visualizing comprises positioning the imaging system to produce an inlet view.

* * * * *